US009254396B2

(12) United States Patent
Mihaylov

(10) Patent No.: US 9,254,396 B2
(45) Date of Patent: Feb. 9, 2016

(54) ADVANCED RADIOTHERAPY TREATMENT PLANNING OPTIMIZATION

(71) Applicant: Rhode Island Hospital, Providence, RI (US)

(72) Inventor: Ivaylo B. Mihaylov, Warwick, RI (US)

(73) Assignee: Rhode Island Hospital, Providence, RI (US)

( * ) Notice: Subject to any disclaimer, the term of this patent is extended or adjusted under 35 U.S.C. 154(b) by 295 days.

(21) Appl. No.: 13/768,015

(22) Filed: Feb. 15, 2013

(65) Prior Publication Data

US 2013/0217948 A1    Aug. 22, 2013

Related U.S. Application Data

(60) Provisional application No. 61/599,605, filed on Feb. 16, 2012.

(51) Int. Cl.
*A61N 5/00* (2006.01)
*A61N 5/10* (2006.01)

(52) U.S. Cl.
CPC .................... *A61N 5/1031* (2013.01)

(58) Field of Classification Search
CPC . A61N 5/1031; A61N 5/1047; A61N 5/1042; G21K 1/025; G06F 19/3481; G06F 19/3437
USPC ............ 600/1; 128/897–899; 378/64, 65, 87, 378/95, 147, 149, 150, 151
See application file for complete search history.

(56) References Cited

U.S. PATENT DOCUMENTS

| | | | |
|---|---|---|---|
| 6,393,096 B1 * | 5/2002 | Carol et al. ................... 378/65 |
| 6,411,675 B1 | 6/2002 | Llacer |
| 6,560,311 B1 | 5/2003 | Shepard et al. |
| 6,719,683 B2 | 4/2004 | Frohlich |
| 6,879,659 B2 | 4/2005 | Alber |
| 6,882,702 B2 | 4/2005 | Luo |
| 7,162,008 B2 | 1/2007 | Earl et al. |
| 7,369,645 B2 | 5/2008 | Lane |
| 7,529,339 B2 | 5/2009 | Goldman et al. |

(Continued)

OTHER PUBLICATIONS

Panayiotis Mavroidis, Georgios A Plataniotis, Magdalena Adamus G'orka and Bengt K Lind, Comments on 'Reconsidering the definition of a dose-volume histogram'—dose-mass histogram (DMH) versus dose-volume histogram (DVH) for predicting radiation-induced pneumonitis, Nov. 22, 2006, Phys. Med. Biol. 51 (2006) L43-L50.*

(Continued)

*Primary Examiner* — Navin Natnithithadha
*Assistant Examiner* — Sunita Reddy
(74) *Attorney, Agent, or Firm* — Mintz Levin Cohn Ferris Glovsky and Popeo, P.C.

(57) ABSTRACT

A method of radiotherapy treatment planning is described. A planned target volume is identified for radiotherapy treatment and at least one volume of interest is identified. The mass, density, and total deposited energy contained in the planned target volume and the volumes of interest are identified and dose objectives are determined. At least one of the objectives is a function of the identified mass, density, or deposited energy. A composite objective function is determined using the dose objectives for the planned target volume and the volumes of interest. A near optimal solution to the composite objective function is determined to produce a radiotherapy treatment plan.

15 Claims, 18 Drawing Sheets

(56) References Cited

U.S. PATENT DOCUMENTS

| | | | |
|---|---|---|---|
| 7,734,010 B2 | 6/2010 | Otto et al. | |
| 7,801,270 B2 | 9/2010 | Nord et al. | |
| 7,835,493 B2 | 11/2010 | Keall et al. | |
| 2002/0080915 A1* | 6/2002 | Frohlich | 378/65 |
| 2004/0001569 A1* | 1/2004 | Luo | 378/65 |
| 2004/0071261 A1* | 4/2004 | Earl et al. | 378/65 |
| 2007/0003011 A1 | 1/2007 | Lane | |
| 2007/0201614 A1* | 8/2007 | Goldman et al. | 378/65 |
| 2009/0041188 A1* | 2/2009 | Keall et al. | 378/65 |
| 2009/0316858 A1* | 12/2009 | Nord et al. | 378/65 |
| 2010/0034357 A1* | 2/2010 | Svesson et al. | 378/152 |
| 2012/0136194 A1* | 5/2012 | Zhang et al. | 600/1 |

OTHER PUBLICATIONS

Aaltonen et al., "Specification of dose delivery in radiation therapy." Recommendation by the Nordic Association of Clinical Physics (NACP). Acta Oncol ; 36 Suppl 10:1-32 (1997).

Chen et al. "Dose Mass—Based IMRT Inverse Planning for Radiotherapy of Thorasic Cancer." *Med. Phys.* 38.6(2011):3686. (Joint AAPM/COMP Meeting Program Abstract #SU-E-T-848).

Nioutsikou et al. "Reconsidering the Definition of a Dose-Volime Histogram." *Phys. Med. Biol.* 50.11(2005):L17-L19.

Spirou et al. "A Gradient Inverse Planning Algorithm with Dose-Volume Constraints." *Med. Phys.* 25.3(1998):321-333.

Wu Q, Mohan R, Niemierko A, et al. "Optimization of intensity-modulated radiotherapy plans based on the equivalent uniform dose." Int J Radiat OncolBiol Phys 52:224-235 (2002).

\* cited by examiner

ADVANCED RADIOTHERAPY TREATMENT PLANNING OPTIMIZATION

RELATED APPLICATIONS

This application claims priority to U.S. Provisional Application No. 61/599,605 filed Feb. 16, 2012, the content of which is hereby incorporated by reference.

STATEMENT REGARDING FEDERALLY SPONSORED RESEARCH

Some of the current subject matter was developed with government support under R01 CA163370-01A1 awarded by National Institutes of Health (NIH). The government may have certain rights in the invention.

FIELD OF THE INVENTION

The invention provides methods for radiotherapy treatment planning that provides dose reduction to healthy tissue while also allowing delivery of curative radiation doses to cancerous tissue.

BACKGROUND

Radiation therapy or radiotherapy is the medical use of ionizing radiation, generally as part of cancer treatment to control or kill malignant cells. Radiation therapy may be curative in a number of types of cancer. It may also be used as part of curative therapy, to prevent tumor recurrence after surgery to remove a primary malignant tumor (for example, early stages of breast cancer). Radiation therapy has been used before, during, and after chemotherapy in susceptible cancers.

Radiation therapy is commonly applied to the cancerous tumor because of its ability to control cell growth. Ionizing radiation works by damaging the DNA of exposed tissue leading to cellular death. Normal tissues (such as skin or organs which radiation must pass through in order to treat the tumor), also receive radiation dose causing cellular damage and death which leads to sometimes serious side effects.

SUMMARY

A method for radiotherapy treatment planning is presented which minimizes the radiation doses to certain masses, rather than volumes, of healthy tissue.

Various aspects of the invention may provide one or more of the following capabilities.

A method of radiotherapy treatment planning is described. A planned target volume is identified for radiotherapy treatment and at least one volume of interest is identified. The mass contained in the planned target volume and the volumes of interest are identified and dose objectives are determined. At least one of the objectives is a function of the identified mass or density. A composite objective function is determined using the dose objectives for the planned target volume and the volumes of interest. A near optimal solution to the composite objective function is determined to produce a radiotherapy treatment plan.

In one embodiment, the function of mass may be:

$$F^k = w^k \sum_{i \in V} f(d_i^{Energy}, d^k) \left( \frac{d_i^{Energy} - d^k}{d^k} \right)^2 \Delta m_i$$

In another embodiment, the function of mass may be:

$$F^k = w^k \sum_{i \in V} f(d_i^{Energy}, d^k) \left( \frac{d_i^{Energy} - d^k}{d^k} \right)^2 \Delta \rho_i$$

In another embodiment, the function of mass may be:

$$mEUD = \left( \sum_{i=1}^{N} \Delta m_i d_i^a \right)^{\frac{1}{a}}$$

In a further embodiment, the function of mass may be:

$$I_j = \sum_{i=1}^{n} D_{i,j} m_{i,j} = \sum_{i=1}^{n} D_{i,j} \rho_{i,j} v_{i,j} = \sum_{i=1}^{n} \frac{E_{i,j}}{\rho_{i,j} v_{i,j}} \rho_{i,j} v_{i,j} = \sum_{i=1}^{n} E_{i,j}$$

In a further embodiment, the radiotherapy treatment plan may include using one of: Intensity Modulated Radiation Therapy, Volumetric Modulated Arc Therapy, Four Dimensional, Adaptive, Real Time Adaptive, Charged Particle Modulated Therapy, Image Guided Radiation Therapy, or particle (photon or charged particle) Energy Modulation.

In a further embodiment, the radiotherapy treatment plan may include using one of: Four Dimensional Intensity Modulated Radiotherapy, Four Dimensional Volumetric Modulated Arc Therapy, or Four Dimensional Intensity Modulated Charged Particle Therapy.

In a further embodiment, the radiotherapy treatment plan may include using one of: Adaptive Four Dimensional Intensity Modulated Radiotherapy, Adaptive Four Dimensional Volumetric Modulated Arc Therapy, or Adaptive Four Dimensional Intensity Modulated Charged Particle Therapy.

In a further embodiment, the radiotherapy treatment plan may include using one of energy modulation for: Intensity Modulated Radiation Therapy, Four Dimensional Intensity Modulated Radiation Therapy, Volumetric Modulated Arc Therapy, Four Dimensional Volumetric Modulated Arc Therapy, Adaptive Intensity Modulated Radiation Therapy, Adaptive Four Dimensional Intensity Modulated Radiation Therapy, Adaptive Volumetric Modulated Arc Therapy, Adaptive Four Dimensional Volumetric Modulated Arc Therapy, Real Time Adaptive Intensity Modulated Radiation Therapy, Real Time Adaptive Four Dimensional Intensity Modulated Radiation Therapy, Real Time Adaptive Volumetric Modulated Arc Therapy, or Real Time Adaptive Four Dimensional Volumetric Modulated Arc Therapy.

In a further embodiment, the radiotherapy treatment plan includes using one of: Real Time Adaptive Four Dimensional Intensity Modulated Radiotherapy, Real Time Adaptive Four Dimensional Volumetric Modulated Arc Therapy, or Real Time Adaptive Four Dimensional Intensity Modulated Charged Particle Therapy.

In a further embodiment, the function of mass is determined from density.

In a further embodiment, the near optimal solution is a clinically acceptable solution.

In a further embodiment, the clinically acceptable solution is a solution in which a dose standard deviation across the planned target volume is less than 4% of dose delivered by the treatment plan.

In a further embodiment, the planned target volume contains at least a portion of a tumor.

In a further embodiment, the at least one volume of interest contains at least a portion of: an organ at risk or an anatomical structure of interest.

In a further embodiment, the planned target volume contains at least a portion of: lung, prostate, head-and-neck, intestine, pancreas, liver, kidney, brain, bone, breast, cervix, colon or thyroid.

In a further embodiment, the invention may be a non-transient computer readable storage medium, comprising executable instructions. The instructions are configured to receive data describing a planned target volume for radiotherapy treatment, at least one volume of interest, the mass contained in the planned target volume and volume of interest, at least one dose constraint for the planned target volume and at least one dose constraint for the volumes of interest. The dose objectives for the planned target volume and the volumes of interest are a function of mass or density. The instructions are further configured to determine a composite objective function from the planned target volume dose objectives and from the dose objectives of the volumes of interest and to determine a near optimal solution to the composite objective function to produce a radiotherapy treatment plan.

In a further embodiment, the executable instructions are configured such that the function of mass is:

$$F^k = w^k \sum_{i \in V} f(d_i^{Energy}, d^k) \left( \frac{d_i^{Energy} - d^k}{d^k} \right)^2 \Delta m_i$$

In a further embodiment, the executable instructions are configured such that the function of density is:

$$F^k = w^k \sum_{i \in V} f(d_i^{Energy}, d^k) \left( \frac{d_i^{Energy} - d^k}{d^k} \right)^2 \Delta \rho_i$$

In a further embodiment, the executable instructions are configured such that the function if mass is:

$$mEUD = \left( \sum_{i=1}^{N} \Delta m_i d_i^a \right)^{\frac{1}{a}}$$

In a further embodiment, the executable instructions are configured such that the function of mass is:

$$I_j = \sum_{i=1}^{n} D_{i,j} m_{i,j} = \sum_{i=1}^{n} D_{i,j} \rho_{i,j} v_{i,j} = \sum_{i=1}^{n} \frac{E_{i,j}}{\rho_{i,j} v_{i,j}} \rho_{i,j} v_{i,j} = \sum_{i=1}^{n} E_{i,j}$$

In a further embodiment, the invention may be a system for radiation treatment planning. The system has an input module for specifying input parameters such as a planned target volume, at least one volume of interest, mass contained in at least one of the planned target volume and the at least one volume of interest, at least one dose constraint for the planned target volume, and at least one dose constraint for the at least one volume of interest. The at least one dose constraint for the planned target volume and the at least one dose constraint for the at least one volume of interest is a function of mass. The system further has a processor configured to determine a composite objective function using the input parameters and to determine a near optimal solution to the composite objective function for the production of a radiotherapy treatment plan.

These and other capabilities of the invention, along with the invention itself, will be more fully understood after a review of the following figures, detailed description, and claims.

DETAILED DESCRIPTION

Figure 1A:
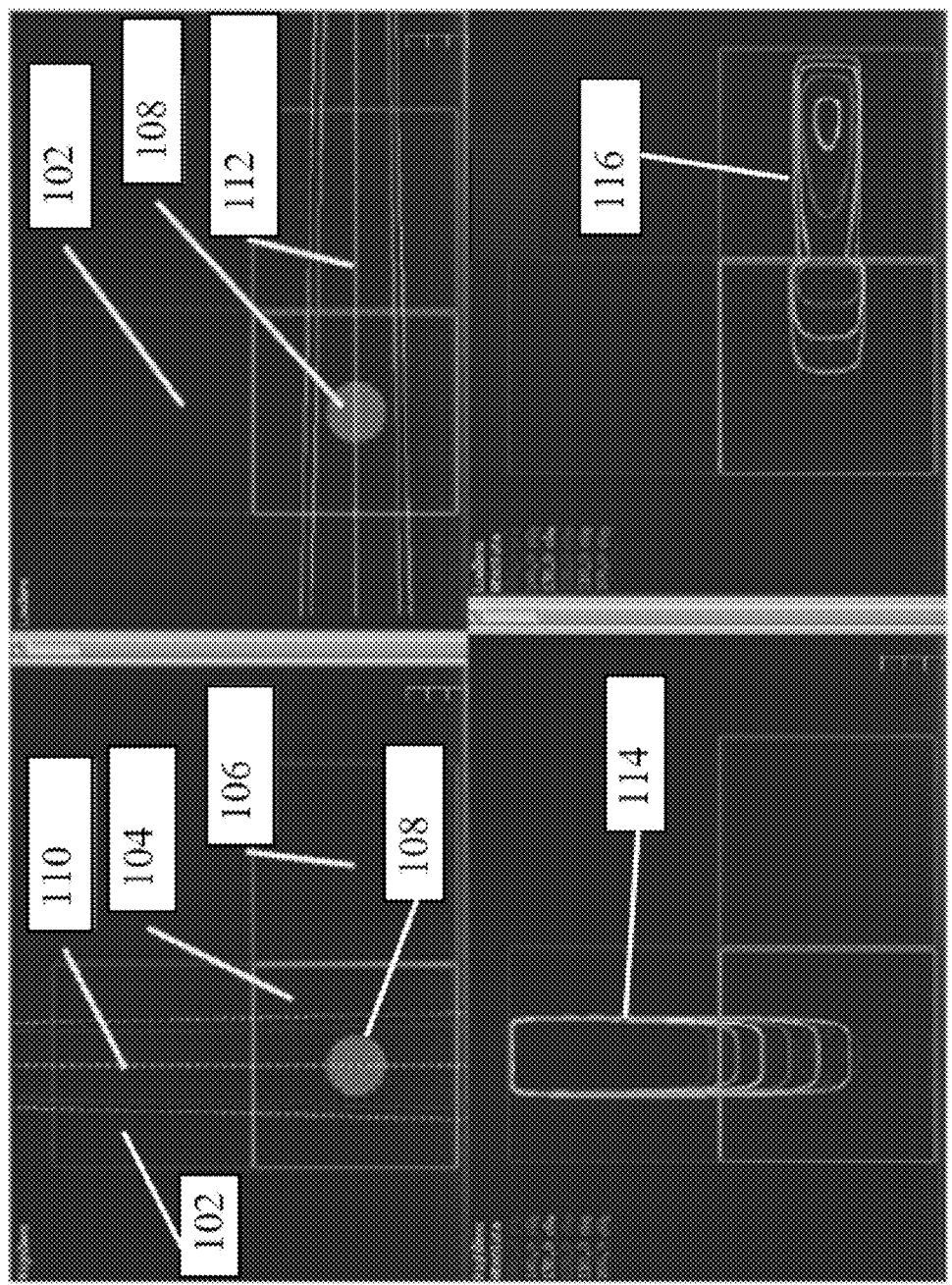
FIG. 1A is an illustration showing the setup of an illustrative radiation therapy example.

High doses of radiation can cause varying side effects during treatment, in the months or years following treatment, or after re-treatment. The nature, severity, and longevity of side effects depends on the organs that receive the radiation, the treatment itself such as type of radiation, dose, fractionation, concurrent chemotherapy, and the patient. The following are a few examples of side effects which may occur from radiotherapy.

Epithelial surfaces may sustain damage from radiation therapy. Depending on the area being treated, this may include the skin, oral mucosa, pharyngeal, bowel mucosa and ureter. If the head and neck area is treated, temporary soreness and ulceration commonly occur in the mouth and throat. If severe, this can affect swallowing, and the patient may need painkillers and nutritional support/food supplements. The esophagus can also become sore if it is treated directly, or if it receives a dose of collateral radiation during treatment of lung cancer. The lower bowel may be treated directly with radiation, as occurs during treatment of rectal or anal cancer, or be exposed by radiation therapy to other pelvic structures such as prostate, bladder, and female genital tract. Typical symptoms are soreness, diarrhea, and nausea.

As part of the general inflammation that occurs, swelling of soft tissues may cause problems during radiation therapy. This is a concern during treatment of brain tumors and brain metastases, especially where there is pre-existing raised intracranial pressure or where the tumor is causing near-total obstruction of a lumen (e.g., trachea or main bronchus). Infertility may also occur. The gonads (ovaries and testicles) are very sensitive to radiation.

Late side effects occur months to years after treatment and are generally limited to the area that has been treated. They are often due to damage of blood vessels and connective tissue cells. Fibrosis and epilation (hair loss) may occur. Dry mouth, or xerostomia, and dry eyes, or xerophthalmia, can become irritating long-term problems and severely reduce the patient's quality of life. Similarly, sweat glands in treated skin, such as the armpit, tend to stop working Lymphedema, a condition of localized fluid retention and tissue swelling, can result from damage to the lymphatic system sustained during radiation therapy. It is a commonly reported complication in breast radiation therapy patients who receive adjuvant axillary radiotherapy following surgery to clear the axillary lymph nodes.

Radiation is a potential cause of cancer, and secondary malignancies. It usually occurs 20-30 years following treatment, although some haematological malignancies may develop within 5-10 years. The cancer occurs within the treated area of the patient. Radiation has potentially excess risk of death from heart disease seen after some past breast cancer radiotherapy regimens.

Malignant lung tumors are the most prevalent form of cancer, affecting more than 219,000 people in the United States and more than 1.35 million people worldwide annually. In the United States alone, lung cancer kills approximately 160,000 individuals yearly—more people than breast, colon and prostate cancers combined. Worldwide more than 1.1 million people succumb to this deadly disease each year. The 5-year control rates for non-small cell lung cancer (NSCLC) are approximately 15% for stages III-IV, and slightly better for stages I-II. It has been shown that local disease control, using conventionally fractionated dose regimens, has not improved in more than a decade.

Healthy tissue toxicity very often is the dose limiting factor, preventing the delivery of therapeutic doses required for a definitive treatment. Symptomatic radiation induced lung injury (RILI) occurs in more than 30% of the patients, while radiologic evidence for RILI occurs in more than half of the cases. Increased healthy tissue toxicity has been correlated with both manual lymphatic drainage (MLD) and local doses. Healthy tissue toxicity may be affected by interaction between irradiated organs such as the heart and lung, implying that planning and delivery techniques for minimizing radiation doses to all critical structures in the region of radiation are crucial for successful curative treatments and minimizing radiogenic late effects such as second cancers.

Another challenging group of cancer patients includes head-and-neck squamous cell carcinoma (HNSCC) cases. Radiotherapy combined with concurrent chemotherapy has a category 1 level of consensus from the National Comprehensive Cancer Center Network Head and Neck Panel. Although various meta-analyses have clearly shown that delivering chemotherapy and radiotherapy concomitantly (chemoradiation) significantly boosts the effects of radiation alone, this approach raises a number of practical challenges, most of them resulting from poor treatment tolerance and reduced compliance to the prescribed dose levels of chemoradiation.

Most HNSCC patients receiving high-dose radiotherapy are affected by severe acute side effects, including mucositis (stomatitis), dysphagia, and skin toxicity (radiation dermatitis). Chemoradiation is associated with an even higher incidence of severe (grade 3/4) acute adverse events, indicating again the detrimental effects of chemo-radiotherapy combination for this treatment site. Although it has been repeatedly substantiated that combining radiotherapy with cisplatin, 5-FU, or mitomycin C yielded the best overall survival data, it can be claimed that the therapeutic potential of these drugs has been taken to its limit.

An important avenue of research refers to advances in radiotherapy planning and delivery and, in particular, intensity-modulated radiotherapy (IMRT). Compared with conventional techniques IMRT allows better sparing of unaffected tissues. The subsequent reduction in radiation-induced mucositis and xerostomia may help to decrease the morbidity of intensive concomitant chemoradiotherapy.

Accordingly, there is a pressing need for improved radiation treatment therapy which reduces collateral radiation dose to healthy tissue.

Intensity Modulated Radiation Therapy

Intensity Modulated Radiation Therapy (IMRT) is a radiotherapy technique which delivers a radiation dose to a planned target volume (PTV), such as a tumor, through multiple beams of varying angles and intensities. This is done in attempt to reduce collateral radiation dose to any nearby organs at risk (OARs). This technique provides a desired cumulative dose to the PTV while spreading the collateral dose over several volumes of interest (VOIs) containing the OARs. The specific configuration of beam sizes, locations and intensities for an individual patient is known as a treatment plan.

IMRT treatment plans may be designed using an inverse planning process. IMRT planning is formulated as an OAR based constraint optimization problem. The radiation dose delivered to a given OAR can be described by the objective function wherein the variables of the function are the parameters of the radiation beams. Objectives are applied such as minimum and maximum allowable dose to the PTV and OARs respectively. The constraint optimization problem can be solved using known mathematical methods such as, but not limited to, gradient evaluation, linear programming, quadratic programming, and linear-fractional programming. The dimensionality of such an objective function can be very high depending on the number of beams used in a given IMRT treatment plan.

For instance, if a patient has lung cancer, an example formulation may be to maximize the dose to the cancer subject to the following objectives: dose to 33% of the heart volume below 3500 cGy, as well as healthy lung dose to 20% of the volume being less than 2000 cGy. In this example, the cancer is the PTV, and the heart and healthy lung are OARs which are contained in VOIs. This example is not limiting, the dosage and portion of OAR may be any acceptable value. The objective of "dose to 33% of the heart below 3500 cGy" is known as a volume-based objectives. By combining multiple volume-based objectives, the expected distribution of the radiation dose can be described. This distribution is typically depicted for clinical purposes as a dose-volume histogram (DVH). The purpose of a DVH is to summarize three dimensional dose distributions in a graphical two dimensional format. The PTV and VOIs are divided into unit voxels and it is assumed that for a given beam intensity, an equal amount of radiation dose is delivered to each voxel within the beam path. A drawback of the volume-based objective and DVH methodology is that it offers no spatial information; i.e., a volume-based objective does not consider, nor does the DVH show, where within a structure a dose is received. Therefore, a more accurate objectives and representation of the dose delivered to a PTV and VOI would be beneficial.

General Physical Principles

The electron density of a medium governs the number of Compton interactions a photon traversing the media undergoes. The electrons, set in motion due to those Compton interactions, lead to ionizations, which affect the underlying biological response in living organisms such as causing DNA damage and cellular death. The higher the density of a media, the more energy is imparted to that media by radiation.

Dose is the radiation energy imparted per unit mass of material. Electron density, which scales with physics density of the material, may be mapped using a computed tomography (CT) scan through a calibration procedure. Using the electron density, the integral dose $I_j$ to an organ j can be expressed as:

$$I_j = \sum_{i=1}^{n} D_{i,j} m_{i,j} = \sum_{i=1}^{n} D_{i,j} \rho_{i,j} v_{i,j} = \sum_{i=1}^{n} \frac{E_{i,j}}{\rho_{i,j} v_{i,j}} \rho_{i,j} v_{i,j} = \sum_{i=1}^{n} E_{i,j} \quad (1)$$

where $D_{i,j}$, $m_{i,j}$, $\rho_{i,j}$, and $E_{i,j}$ are the radiation dose, mass, density, volume, and imparted energy in the voxel i of an organ j.

Mass Based Optimization

It follows from equation (1) that if the sum is minimized, in essence the total energy $$\sum_{i=1}^{n} D_{i,j} m_{i,j}$$

imparted on the organ j will be minimized. Furthermore, since the radiation dose is dependent on the energy of the incident radiation, equation 1 can be used also to optimize the energy modulation of that incident radiation, such that the total energy $I_j$ to a VOI is minimized. In other words, if radiation beams are directed through lower density regions, for the same dose to the targets, less dose is delivered in low density media as compared to high density media. Thus, a more accurate representation of the dose delivered to a PTV and VOI is provided and can be leveraged to develop a treatment plan that provides lower collateral dose while still providing a curative dose to the PTV.

Illustrative Example

The effect of mass based optimization is illustrated in FIG. 1A. On the top left is presented the experimental set-up. There are three cubic volumes of interest, each with a size of 10×10× 10 cm³. VOIs 102, 104 and 106 have densities of 0.8, 1.0, and 0.2 g/cm³ respectively. In the middle of VOI 102 there is a target 108, representing the PTV. The PTV (a 3 cm long cylinder with a diameter of 3 cm) is irradiated twice: 1) through an anterior posterior (AP) beam 110 traversing the higher (0.8 g/cm³) density VOI 102, and 2) through a lateral beam 112 traversing the lower (0.2 g/cm³) density VOI 106. Either beam is isocentric, i.e. the isocenter is centered on the PTV, with an area at the isocenter of 5×5 cm². Each beam is normalized such that the average dose to the PTV from that beam is a 100 cGy. The bottom left panel of FIG. 1A shows an isodose comparison, where the set of contour lines 114 correspond to doses of 150, 140, 130, 120, 110, and 100 cGy. The interior contour lines represent the higher dose values.

Figure 1B:
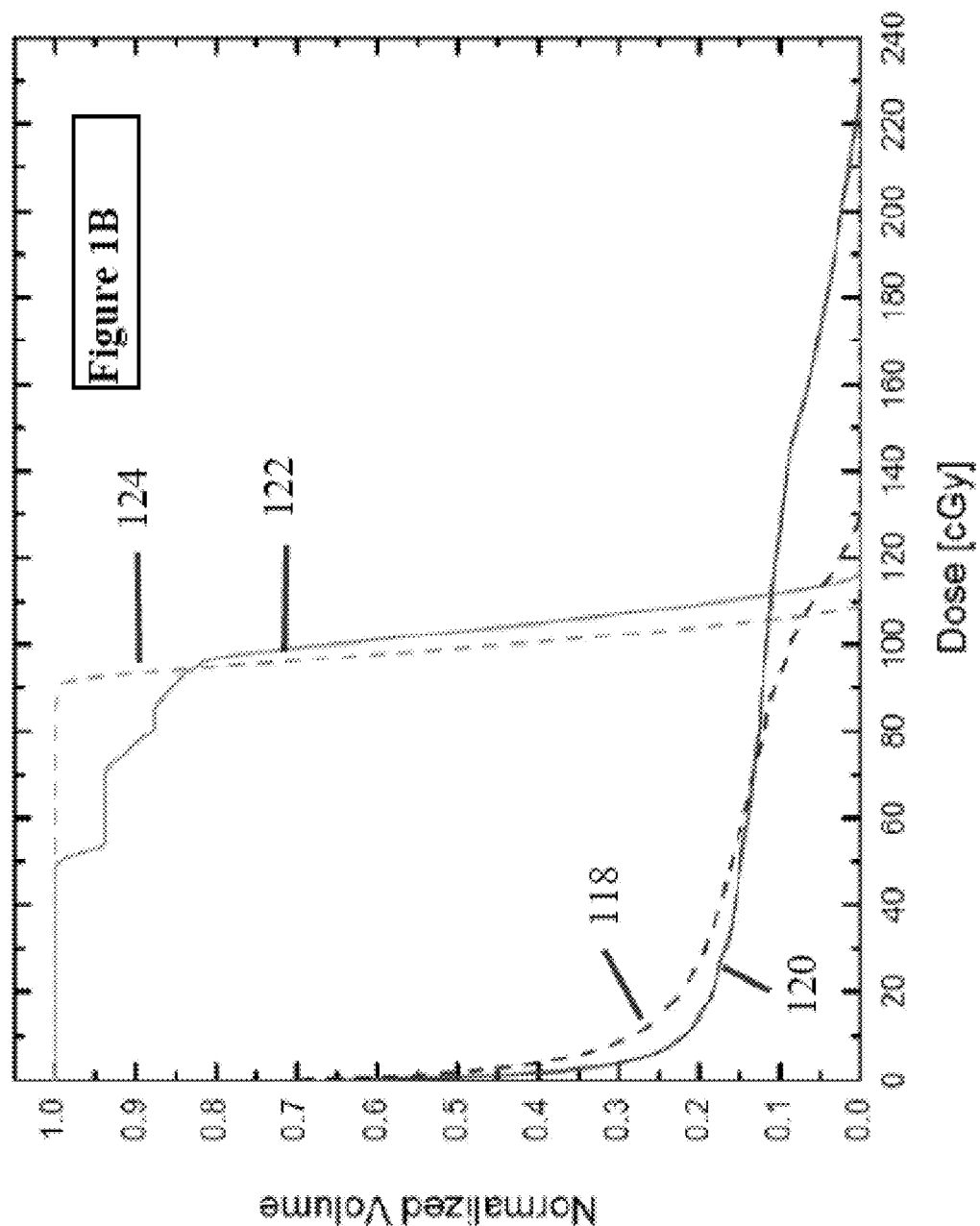
FIG. 1B is a plot illustrating dose volume histograms (DVHs) of the experimental set up from FIG. 1A.

On FIG. 1B the corresponding DVHs are presented. For a normalized volume in the example scenario, lines 122 and 124 represent the dose delivered to the PTV from the AP and Lat beams respectively. Lines 118 and 120 represent the dose delivered to the VOIs 102 and 106 respectively. As shown in FIG. 1B, the mean dose 118 to the low density VOI 106 is 20.5 cGy, while the mean dose 120 to the high density VOI 102 is 25.2 cGy. Therefore, irradiating the PTV through the lower density VOI 106 results in the same average dose to the target, while delivering ~23% lower average dose to VOI 106 compared to the higher density VOI 102.

In other words, delivering dose to a PTV through low density VOIs facilitates the dose deposition to the PTV by the virtue of less material attenuating the beam as well as lower dose deposited to the low density VOI because of the lack of scattering events in this low density media.

Optimizing a treatment plan based on the masses of the VOIs in the example will reduce the intensity of the AP beam through VOI 102 and increase the intensity of the lateral beam through VOI 106. The objective for the optimization is to minimize the dose delivered to both high and low density VOIs. Effectively, for certain target coverage, more radiation would be delivered through low density VOI and less through high density VOI.

Mathematical Framework for Mass Based Optimization

IMRT plans may be designed through an inverse planning process, where the optimization goals are expressed through a number of optimization objectives. The optimization algorithm divides each beam's cross-sectional plane into a two dimensional array of finite size beamlets. Each beamlet is assigned a weight. The weights may be optimized such that two dimensional intensity maps of variable intensities are created. Summation of the radiation coming from all beamlets through those intensity maps, which may be different for each beam, results in generation of optimization functions $F^k$, k=1, . . . , n, where k runs over all the objectives specified for all VOIs. Those optimization functions are a mathematical representation of IMRT optimization goals. The inverse opti mization algorithm attempts to minimize a composite objective function that is expressed as:

$$F(\tau) = \sum_{k=1}^{n} F^k \quad (2)$$

Equation 2 is a sum of all optimization goals and objectives. τ is the set of parameters over which the IMRT solution is optimized. For each VOI there might be none or more than one $F^k$ specified. Minimum and maximum dose optimization functions may be described as:

$$F^k = w^k \sum_{i \in V} f(d_i^{Energy}, d^k) \left( \frac{d_i^{Energy} - d^k}{d^k} \right)^2 \Delta m_i \quad (3)$$

where $f(d_i, d^k) = H(d_i - d^k)$ for maximum dose and $f(d_i, d^k) = H(d^k - d_i)$ for minimum dose. $H(d_i - d_k)$ denotes a Heaviside step function. V denotes the volume of the VOI for which $F^k$ is evaluated, $d_i^{Ephot}$ is the dose, dependent on the energy of the incident radiation Ephot, in voxel, three dimensional volume element, i, and $d^k$ is the desired dose, either minimum or maximum, in each voxel. $m_i$ denotes the mass of the ROI contained in voxel i, while $\Delta m_i$ is the relative, with respect to the total VOI mass, mass in that voxel. Weight $w^k$ is greater than or equal to zero and may be specified to control the importance and prioritize targets and OARs. The minimum and maximum dose mass objectives are evaluated as $F^k$, where in equation 3, V is the volume of the VOI. The optimization problem consists of solving for min, F(τ) where τ>0. The quadratic term in equation 3 makes the function $F^k$ always positive thereby requiring the optimization to find only minimum, i.e. to minimize the differences $d_i^{Energy} - d^k$. The normalization with respect to dose $d^k$ and to total organ volume in the terms $\Delta v_i$ respectively scale the functions $F^k$ uniformly such that the contributions from targets and OARs in F(τ) are of the same magnitude and a global composite objective function (cf. Eq. 2) can be constructed.

Other forms of the optimization functions, including mass explicitly, are described as:

$$mEUD = \left( \sum_{i=1}^{N} \Delta m_i d_i^a \right)^{1/a} \quad (4)$$

Where mEUD is mass weighted equivalent uniform dose, $\Delta m_i$ is the relative mass in dose voxel i, $d_i$ is the dose in that voxle, and a is an organ specific parameter. Values of a may be determined as shown by Wu et al., (Wu Q, Mohan R, Niemierko A, et al. Optimization of intensity-modulated radiotherapy plans based on the equivalent uniform dose. Int J Radiat Oncol Biol Phys 2002; 52:224-235) the entirety of which is incorporated herein by reference. The actual form of the optimization function F(mEUD) which would be minimized is formulated as:

$$F(mEUD) = \theta(mEUD, mEUD_0) \left( \frac{mEUD - mEUD_0}{mEUD_0} \right)^2 \quad (5)$$

Where $mEUD_0$ is the desired objective level, and $\theta(mEUD, mEUD_0)$ is $H(mEUD - mEUD_0)$, 1, and $H(mEUD_0 - mEUD)$ for maximum, target, and minimum mEUD, respectively.

Furthermore, instead of $m_i$ or $\Delta m_i$ the density $\rho_i$ can be also used in the objective functions, thereby allowing density based optimization.

Mass based optimization as described in the above mathematical framework is capable of considerable dose reduction to healthy tissue. Utilization of the lower healthy tissue doses to achieve isotoxic dose escalation in majority of the cancer cases can substantially, 20% to 40%, and even further, increase the tumor control probability, and therefore allow the delivery of definitive curative radiation doses for patients, who have lower chances of cure with current standard-of-care techniques.

Optimization of Illustrative Example

Figure 2A:
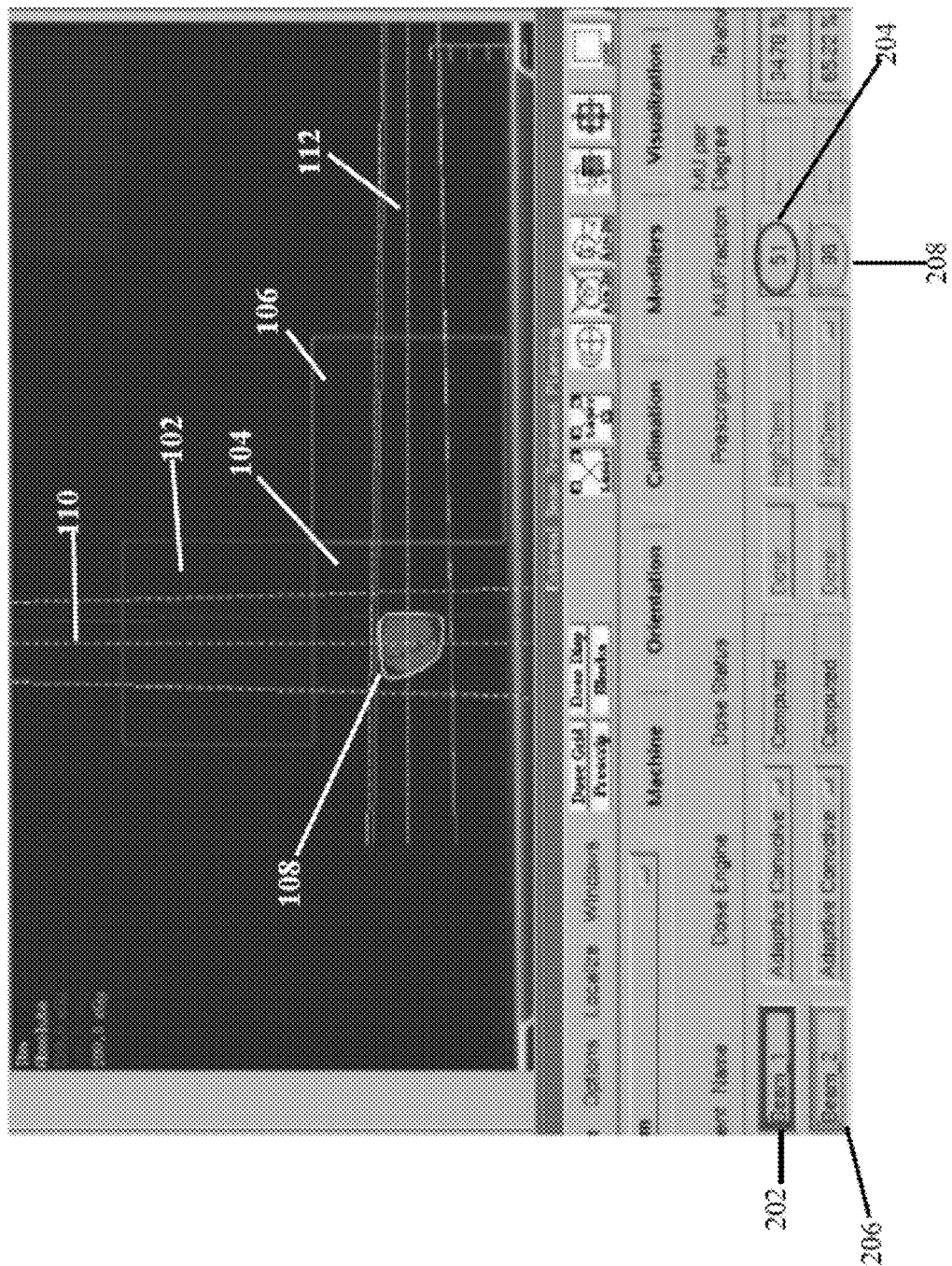
FIG. 2A is an illustration showing the results of optimizing the illustrative example treatment plan from FIG. 1A.

Returning to the illustrative example shown on FIG. 1A, a mass based optimization was performed. The optimization cost function is described by equation 3. The objective was to deliver 100 cGy to the PTV through only two IMRT segments with an AP (110) and Lat (112) beams as depicted on FIG. 2A. The planned monitor units (MUs) are denoted by 204 and 208. A Monitor Unit is a unit of measure of the energy output of a radiotherapy machine and is directly proportional to dose. The delivered 96 MUs (i.e. deposited energy) through the low density VOI (106) is almost twice the 51 MUs deposited through the high density VOI (102). If radiation beams are directed through lower density regions, for the same dose to the targets, less dose is delivered in low density media as compared to high density media.

The described embodiment was realized as a software add-on to the Pinnacle treatment planning system, from Philips Radiation Oncology Systems, Fitchburg, Wis. Pinnacle is a highly specialized software program for external beam radiotherapy. Pinnacle employs a gradient descent algorithm for solving the composite objective function (e.g., cost function).

Figure 2B:
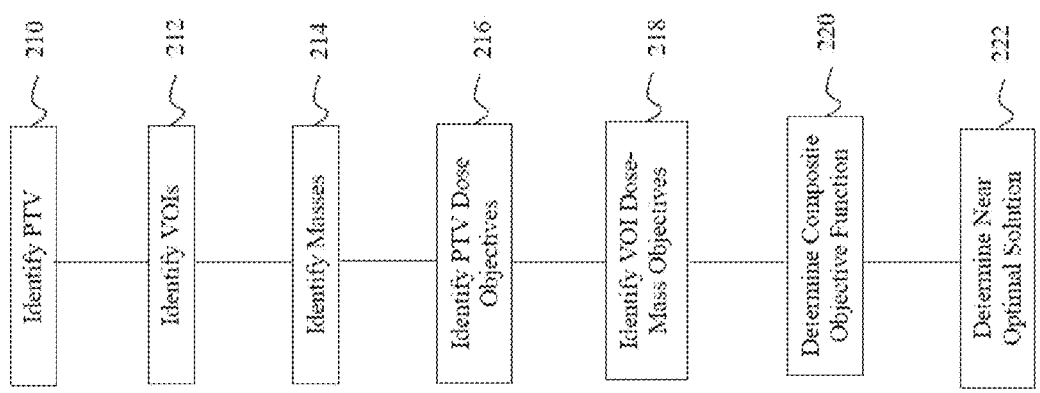
FIG. 2B illustrates the method steps to produce a radiotherapy treatment plan in accordance with one embodiment.

FIG. 2B illustrates the method steps to produce a radiotherapy treatment plan in accordance with an embodiment of the invention. Step 210 comprises identifying the PTV. Step 212 comprises identifying the VOIs. Step 214 comprises identifying any necessary PTV and VOI masses. This may be done, for example, by using a CT scanner. Step 216 comprises identifying PTV dose objectives and step 216 comprises identifying VOI dose objectives. Step 220 comprises determining a composite objective function which contains all of the dose objectives for the PTV and VOI in a format such that it is ready for optimization. Step 222 comprises solving the objective function for a near optimal solution. Solving for the minimum of the objective function may be subject to constraints of a particular mode or form of radiation therapy and a particular radiation therapy device. The near optimal solution may be a degenerate solution which satisfies some acceptable clinical criteria.

Figure 2C:
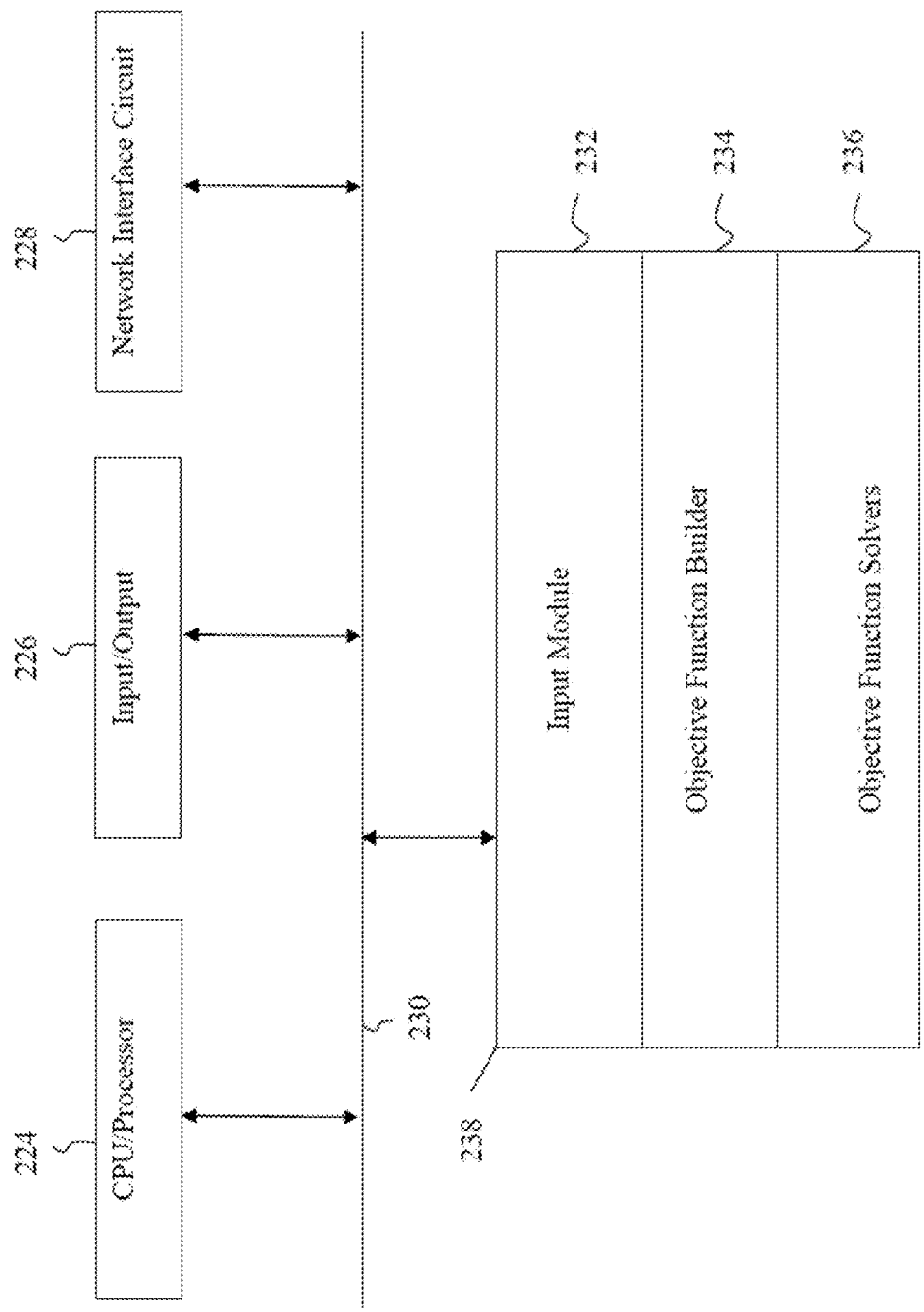
FIG. 2C illustrates a computer system configured to perform operations to produce a radiotherapy treatment plan in accordance with another embodiment of the invention.

FIG. 2C illustrates a computer system configured to perform operations to produce a radiotherapy treatment plan in accordance with another embodiment of the invention. The computer system comprises standard components, such as a central processing unit 224 and input/output devices 226 connected via a bus 230. The input/output devices may include a keyboard, mouse, display, printer and the like. A network interface circuit 228 may also be connected to the bus 230 to provide connectivity to a network (not shown). A memory 238 is also connected to the bus. The memory 238 stores executable instructions to implement operations of the invention. For example, the memory 238 may store an input module 232 for receiving and specifying parameters. The objective function builder 234 collects the parameters and builds a suitable composite objective function in accordance with the invention. The objective function solvers 236 implement solving algorithms to produce a near optimal solution to the objective function and provide a radiotherapy treatment plan.

SPECIFIC EXAMPLES

The radiotherapy treatment planning method was applied to one lung and one head-and-neck (HN) case to provide illustrative examples of the effects of mass- and energy-based optimization treatment planning methods. For each example, three IMRT plans are created: one generated with volume based optimization, one generated with mass based optimization, and one generated with energy based optimization. The three plans had the same set-up, (i.e. beam directions, dose grid resolution, machine parameters used for IMRT optimization) and same prescription doses to 95% of the PTV. In the mass-based and energy-based plans, only the PTV objective was designed as volume-based, all other OARs were designed as mass-based or energy-based objectives respectively. In the volume-based plans, the PTV and all OAR objectives were designed as volume-based objectives.

The objective function used for mass-based optimization is described by equation 3. As used herein, energy-based optimization is a type of mass based optimization and is based on equation 1. The objective functions used for volume-based optimization (i.e., for the PTV) is equivalent to equations 3 where the mass variable $m_i$ is replaced with the volume equivalent $v_i$.

For each case, the objectives (min or max dosage to PTV and OARs) were determined and entered into the Pinnacle software add-on (i.e. each variable in equation 3 was specified for each objective including dosage $d^k$ and weights $w^k$) and a clinically acceptable solution was found using Pinnacle's gradient descent inverse optimization solving software. A solution may be deemed clinically acceptable if the standard deviation across the PTV is an acceptable value. Aaltonen et al. has shown, on the basis of analytic tumor control probability calculations, that acceptable values may include values between 0% and 4% of the prescription dose (Aaltonen et al., Specification of dose delivery in radiation therapy. Recommendation by the Nordic Association of Clinical Physics (NACP). Acta Oncol 1997; 36 Suppl 10:1-32). The present invention is not limited by the range of the abovementioned clinically acceptable values for the standard deviation of the dose; other embodiments are within the scope and spirit of the invention as long as they satisfy the patient specific clinical needs.

Example 1

Lung

Treatment was limited to a 100 segments for 9 equally spaced beams. The dose to the PTV was escalated to the maximum possible subject to the following objectives: maximum cord dose below 4500 cGy, dose to 33% of the heart below 3500 cGy, as well as healthy lung dose to 20% and 30% of the volumes being less than 3000 and 2000 cGy respectively. All volume-based mass-based, and energy-based solutions for which the dose standard deviation across the PTV was ~4% of the prescription dose were deemed as clinically acceptable.

The objective functions were interfaced to Pinnacle treatment planning system. The volume-based functions were designed according to a modified version of equation 3, in which volume ($v_i$) replaces mass ($m_i$). Mass-based objective functions were designed according to equation 3 and energy-based objective functions designed according to equation 1. Volume-based objective functions were designed for the PTV in all cases. For the other OARs mass or energy based objectives were used when mass or energy optimization was respectively performed. The dose grid dimensions, position, and voxel size were also the same as in the volume-based optimization. The mass of lung tissue (cf. Equation 3) contained in each dose voxel i was estimated by $m_i = v_i * \rho_i$, where $v_i$ is the VOI contained in the dose voxel, while $\rho_i$ is the average density within the VOI contour intersecting the dose voxel. The average density was estimated from the raw CT data, which consists of voxels with a size of 0.117×0.117×0.3 cm³.

Figure 3A:
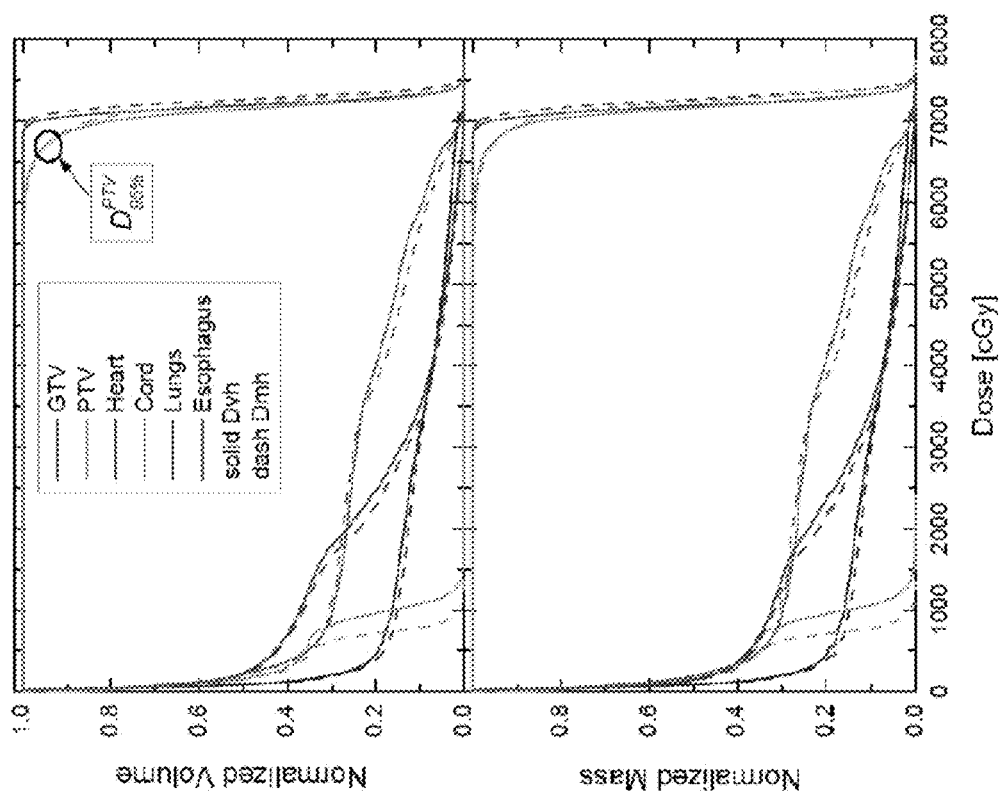
FIG. 3A is a plot illustrating, for a lung example case, a comparison of DVHs (top) for the planned target volume (PTV) and each volume of interest (VOI) from volume- and mass-based optimization plans, as well as a comparison between dose mass histograms (DMHs) derived from volume- and mass-based optimization plans (bottom).
Figure 3B:
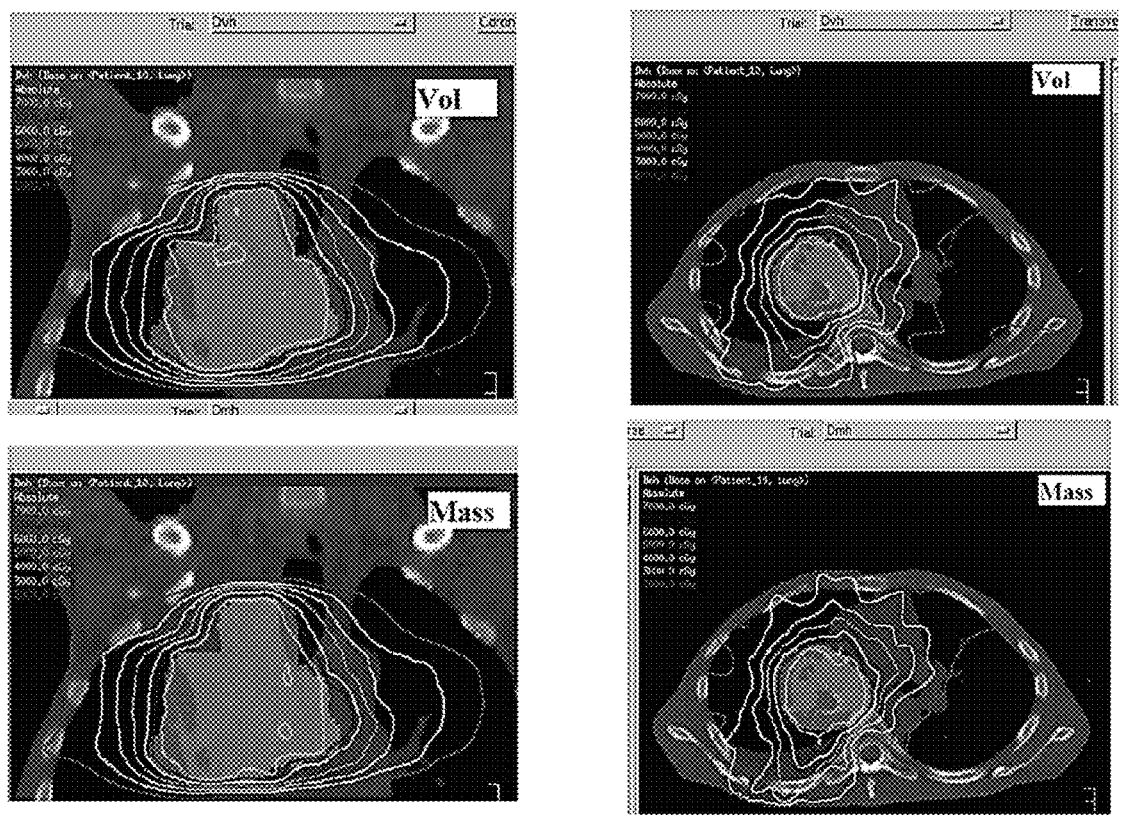
FIG. 3B is a series of plots illustrating isodose distributions for both volume (upper) and mass (lower) based optimization of two cross sections of a lung.

Comparison plots, between volume-based and mass-based optimization results based on DVHs (top) and dose-mass histograms (DMHs, bottom) are presented on FIG. 3A. FIG. 3B is a series of plots illustrating isodose distributions for both volume (top) and mass (bottom) based optimization of two cross sections of lung. The contour lines on the isodose distributions, from inside to outside, correspond to dose levels of 7000, 6500, 6000, 5000, 4000, 3000, and 2000 cGy respectively. It is evident from the isodose plots that 2000 cGy, 3000 cGy and 4000 cGy lines are encompassing less tissue and volumes for mass-based optimization as compared to volume-based optimization.

Figure 3C:
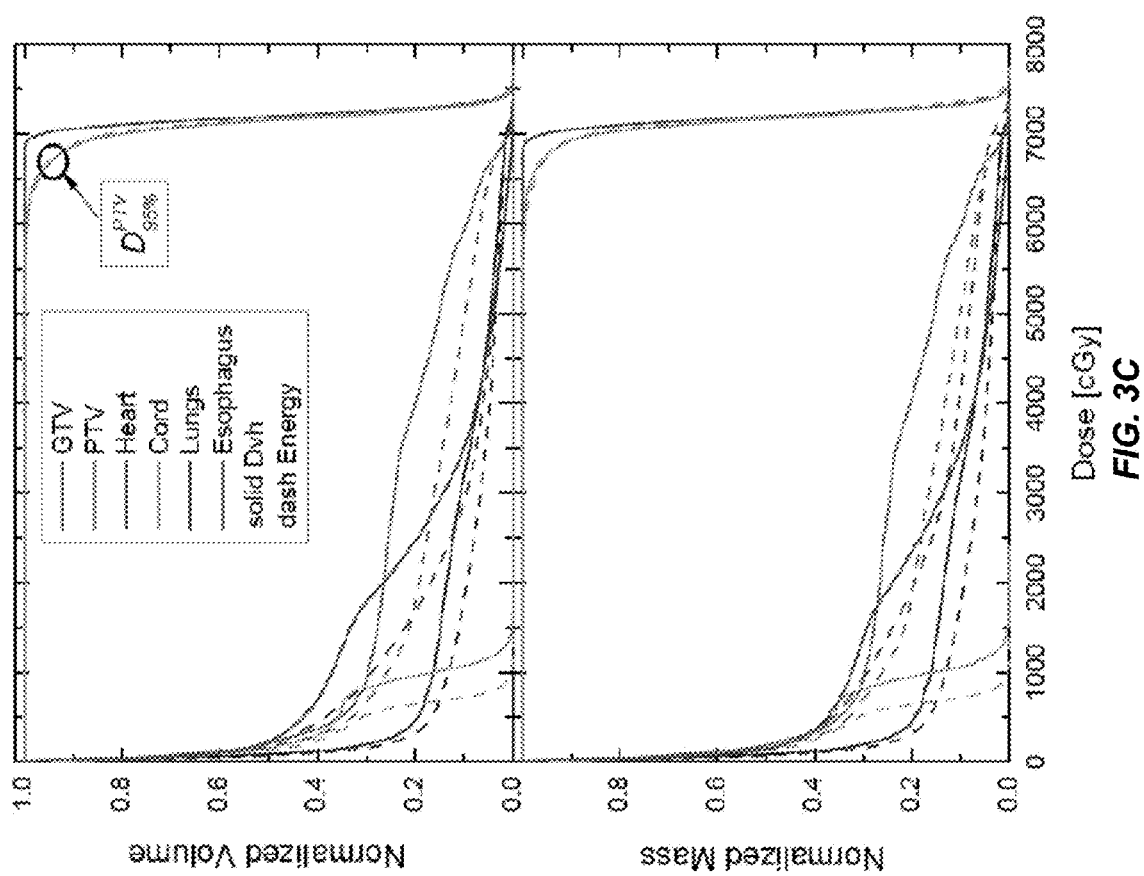
FIG. 3C is a plot illustrating, for a lung example case, a comparison of DVHs (top) and DMHs (bottom) for the PTV and each VOI from volume based and energy based optimization plans.
Figure 3D:
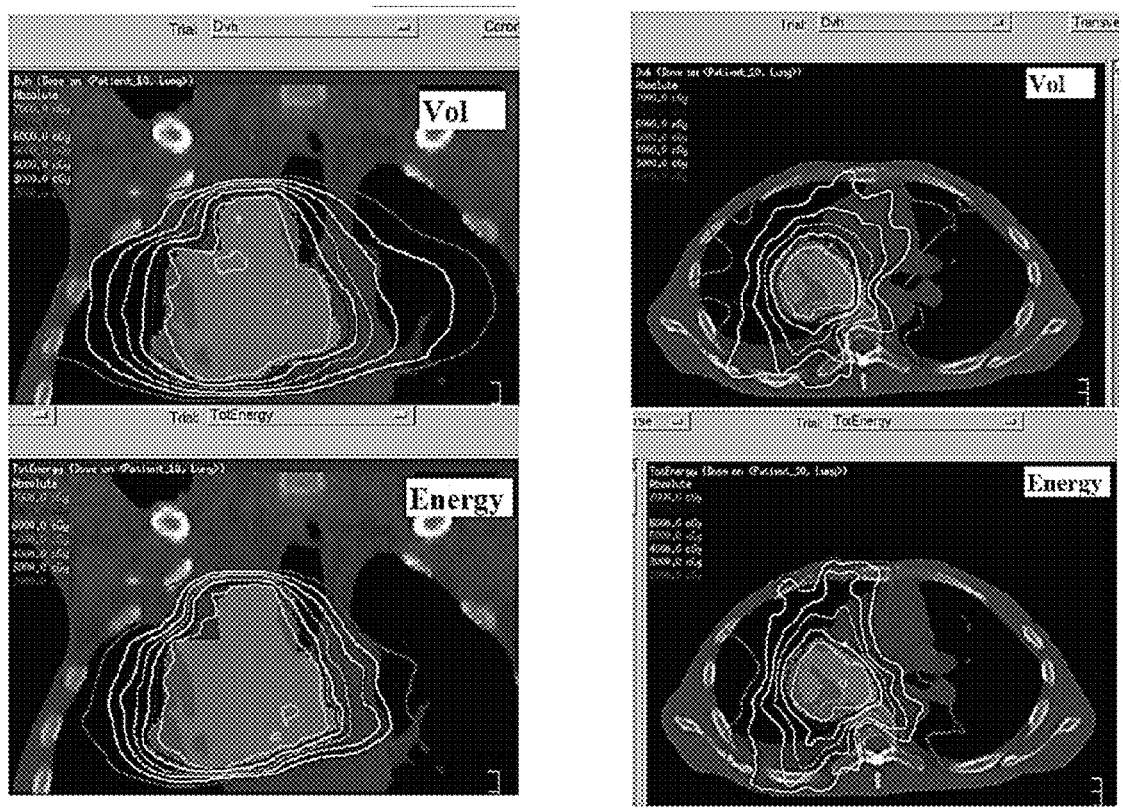
FIG. 3D is a series of plots illustrating isodose distributions for both volume (upper) and energy (lower) based optimization of two cross sections of a lung.

FIGS. 3C and 3D illustrates DVHs, DMHs, and isodose comparisons for the same lung patient as shown in FIG. 3A-B; however, the comparison is between volume and energy based optimization. FIGS. 3C and 3D show reduced radiation dose for collateral tissue when using the energy-based optimization as compared to the volume based optimization.

Example 2

Head and Neck

Treatment was limited to 9 equally spaced split beams (or 18 unsplit beams) and a total of 220 segments. The dose to the PTV was escalated to the maximum possible subject to the following objectives: maximum cord and brainstem doses below 4800 and 5000 cGy respectively, dose to 50% of the larynx below 4000 cGy, as well as dose to 50% of each parotid gland to less than 3000 cGy. In addition, 90% of the intermediate risk nodal volumes were planned for doses 1200 cGy lower than the doses for 95% of the PTVs. If 95% of the PTV was covered by 6600 cGy, then 90% of the intermediate risk Nodal volumes received no less than 5400 cGy. Volume-based, mass-based, and energy-based solutions for which the dose standard deviation across the PTV was ~4% of the prescription dose were deemed as clinically acceptable.

As in the lung example, the objective functions were interfaced to Pinnacle treatment planning system. Mass-based objective functions were designed according to equation 3, while energy-based optimization functions were based on equation 1. The dose grid dimensions, position, and voxel size were also the same as in the volume-based optimization. The mass of tissue (cf. Equation 3) contained in each dose voxel i was estimated by $m_i = v_i * \rho_i$, where $v_i$ is the VOI contained in the dose voxel, while $\rho_i$ is the average density within the VOI contour intersecting the dose voxel. The average density was estimated from the raw CT data, which consists of voxels with a size of 0.117×0.117×0.3 cm³.

Figure 4A:
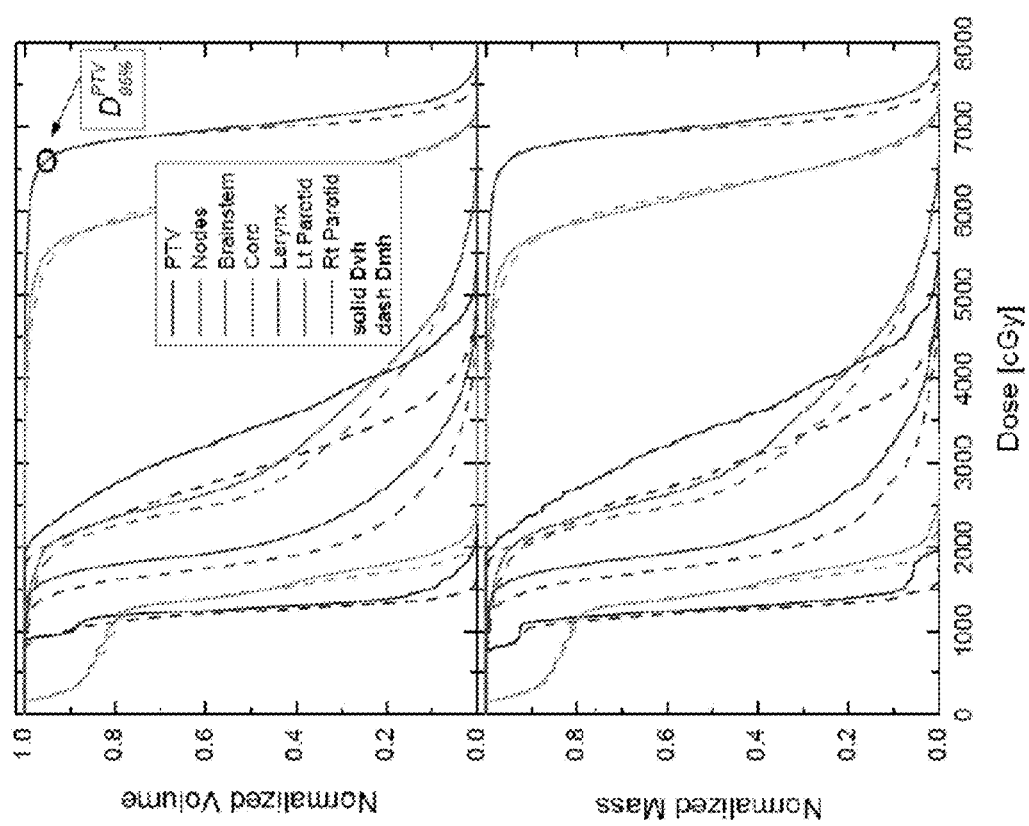
FIG. 4A is a plot illustrating, for a head and neck example case, a comparison of DVHs (top) and DMHs (bottom) for the PTV and each VOI from volume based and mass based optimization plans.
Figure 4B:
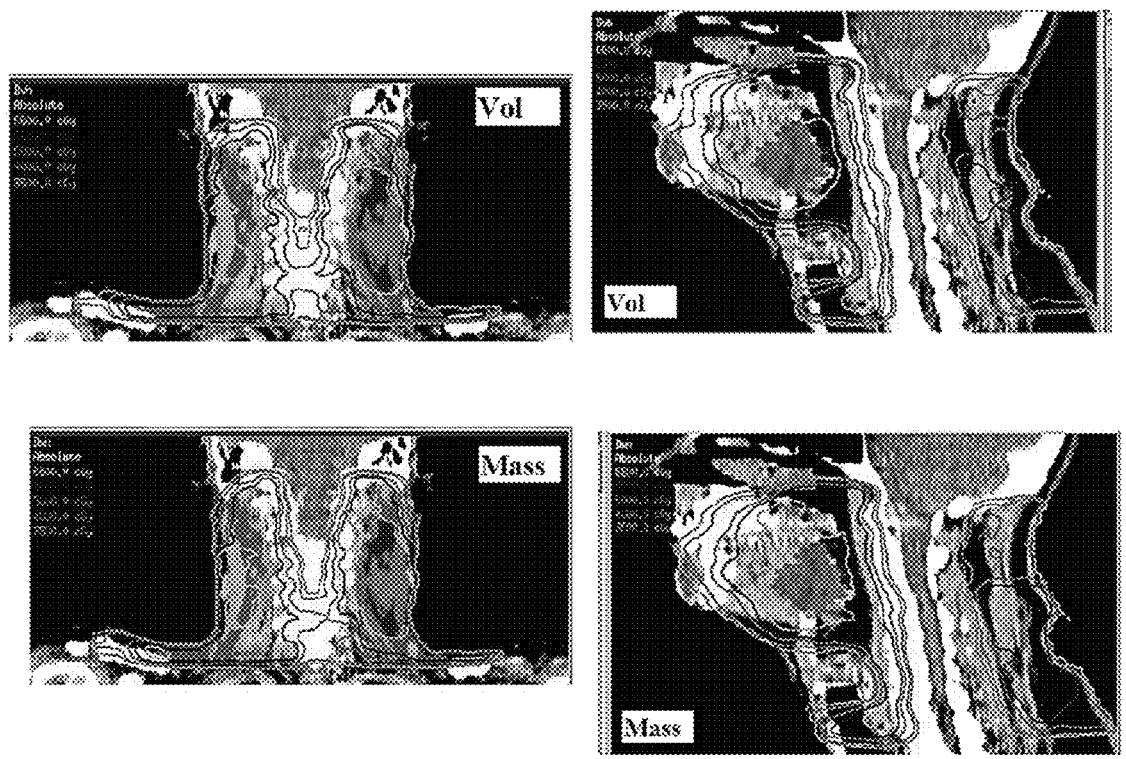
FIG. 4B is a series of plots illustrating isodose distributions for both volume (upper) and mass (lower) based optimization of two cross sections of a head and neck.
Figure 4C:
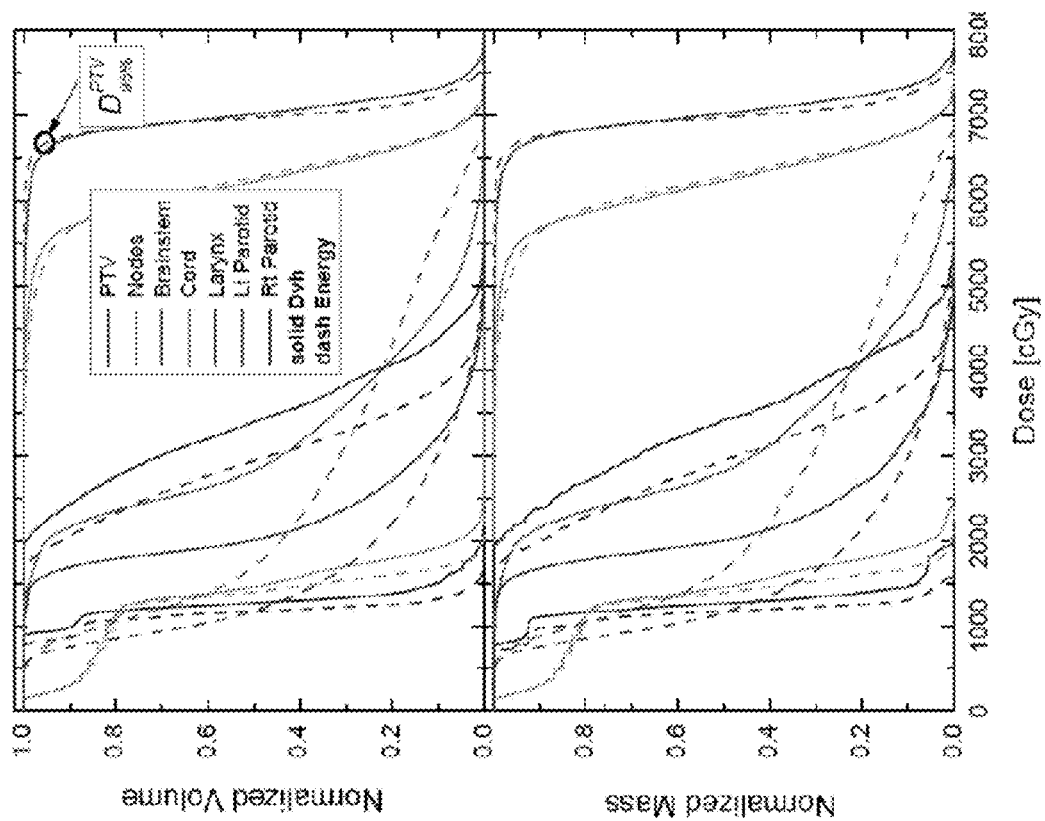
FIG. 4C is a plot illustrating, for a head and neck example case, a comparison of DVHs (top) and DMHs (bottom) for the PTV and each VOI from volume based and energy based optimization plans.
Figure 4D:
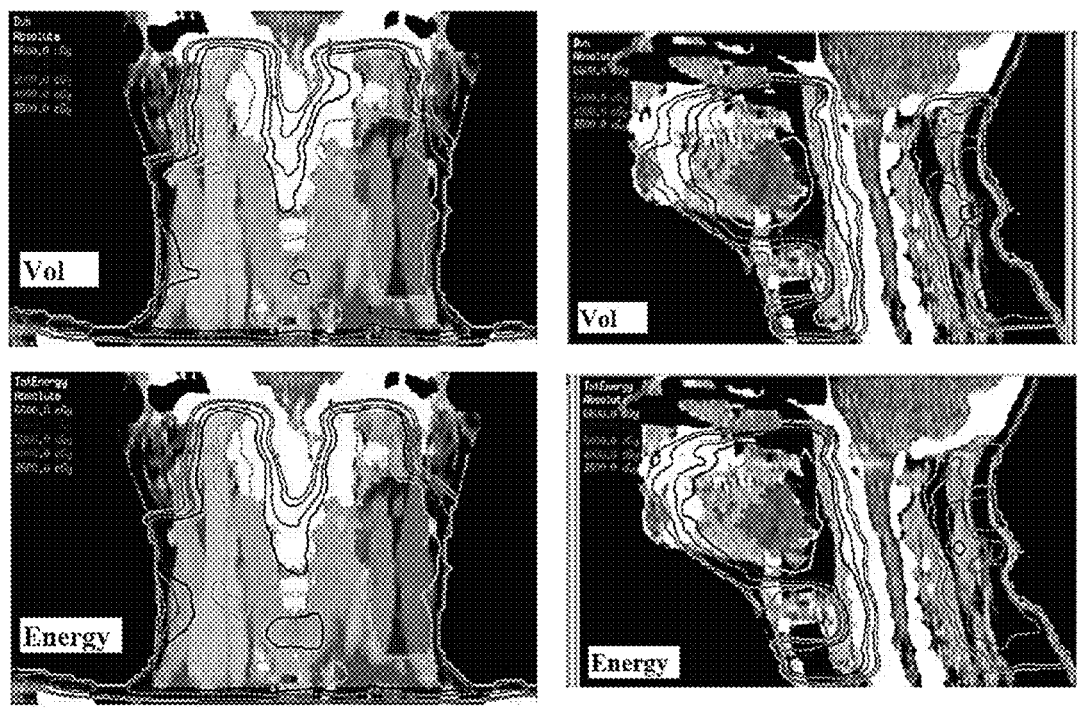
FIG. 4D is a series of plots illustrating isodose distributions for both volume (upper) and energy (lower) based optimization of two cross sections of a head and neck.

Comparison plots, between volume-based and mass-based optimization results based on DVHs, DMHs, and isodose distributions, are presented on FIGS. 4A and 4B. FIG. 4A shows the DVHs (top) and DMHs (bottom) for the PTV and each VOI for volume- and mass-based optimizations. FIG. 4B shows the isodose distributions for volume and mass based optimization of that head and neck patient. The contour lines, from inside to outside, correspond to dose levels of 6600, 6000, 5000, 4000, and 3500 cGy respectively. The 3500 cGy and 4000 cGy isodose lines in mass-based optimization stay further away from the spinal cord and larynx regions with mass based plan as opposed to volume-based plan. It is also clear from FIG. 4A that for equivalent target coverage, mass-based optimization results in lower doses to spinal cord, brainstem, larynx, and parotid glands. FIGS. 4C and 4D illustrate isodose distributions comparing volume-based and energy-based optimizations for the same head-and-neck patient. Energy-based optimization results in lower doses to surrounding healthy tissue than volume-based optimization for identical tumor doses.

Treatment Plan Comparison Mass Vs. Volume

Further validation of the invention was performed on cohorts of lung and HN patients. For each patient case volume-, mass-, and energy-based optimized plans were normalized to deliver the same dose to 95% of the PTV, therefore resulting in clinically equivalent target coverage.

For illustrative purposes, the DVH data derived from the treatment plans was normalized according Equation 6. Those quantities derived from the DVHs are termed dose indices (DIs). A DI is numerically equal to a dose covering a certain absolute or fractional volume of a given anatomical structure. Normalization of the DIs was performed because different patients had different prescription doses and different absolute DIs. A normalized DI greater than unity corresponds to lower OAR dose for mass- or energy-based optimization and vice versa.

$$\Delta DI^{CAR}_{fractional\ volume} = \frac{D^{OAR}_{Volume-based, fractional\ volume}}{D^{OAR}_{Mass-based, fractional\ volume}} \quad (6)$$

Figure 5A:
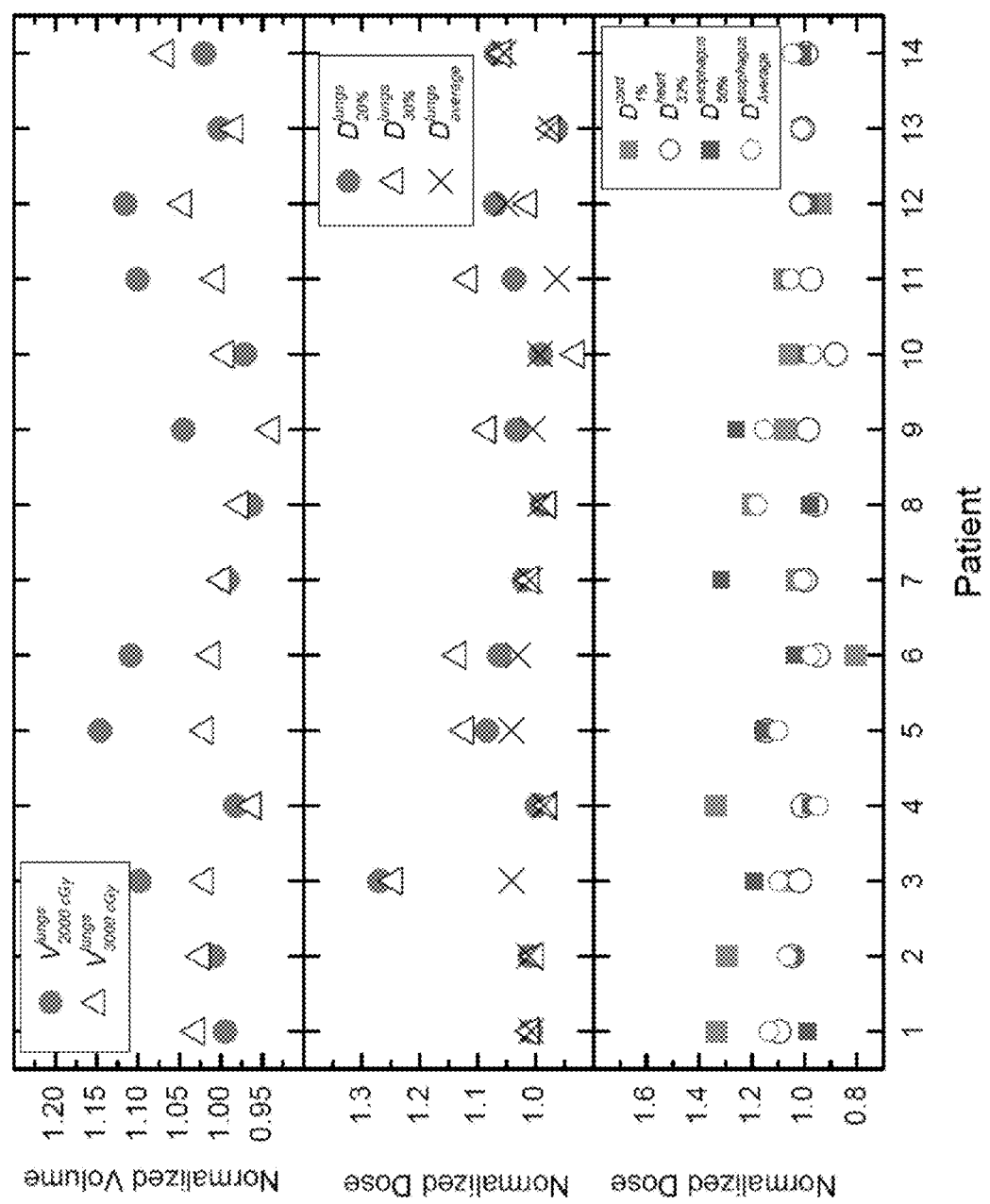
FIG. 5A is a plot illustrating normalized dose indices, average doses, and isodose volumes for 14 lung cases for both volume and mass based optimization plans.

FIG. 5A outlines the differences between the volume- and mass-based optimization schemes for the OARs in the lung cancer cases. The standard deviations of the doses across the PTV are ranging from 2.9% to 4.11%, with an average 3.68% for mass-based optimization and from 2.8% to 4.2%, with an average 3.65% for volume-based optimization, indicating virtually equivalent dose homogeneity across the PTV. The plotted quantities on the figure are normalized dose indices (DI) and volume indices (VI). VIs are similar to DIs described above and they represent the volume of anatomical organ encompassed by a certain isodose line. Normalized DIs and the VIs are calculated according to Equations 6 and 7:

$$\Delta VI^{OAR}_{iso\ volume} = \frac{V^{OAR}_{Volume-based, iso\ volume}}{V^{OAR}_{Mass-based, iso\ volume}} \quad (7)$$

It is evident from FIG. 5A that majority of DIs are greater or equal than unity. On average, over the 14 lung cases, the achievable sparing of ~14.1% for the maximum dose to the spinal cord, ~1% for one third of the heart volume, and ~7.1% to 50% of esophageal volume with mass-based optimization is achieved. The doses to 20% and 30% of the lung volumes are on average ~4.5-5.0% lower with mass-based optimization. These findings indicate that with mass-based objective optimization function, lower population-based doses are achieved for lung cases for equivalent doses delivered to tumors.

Figure 5B:
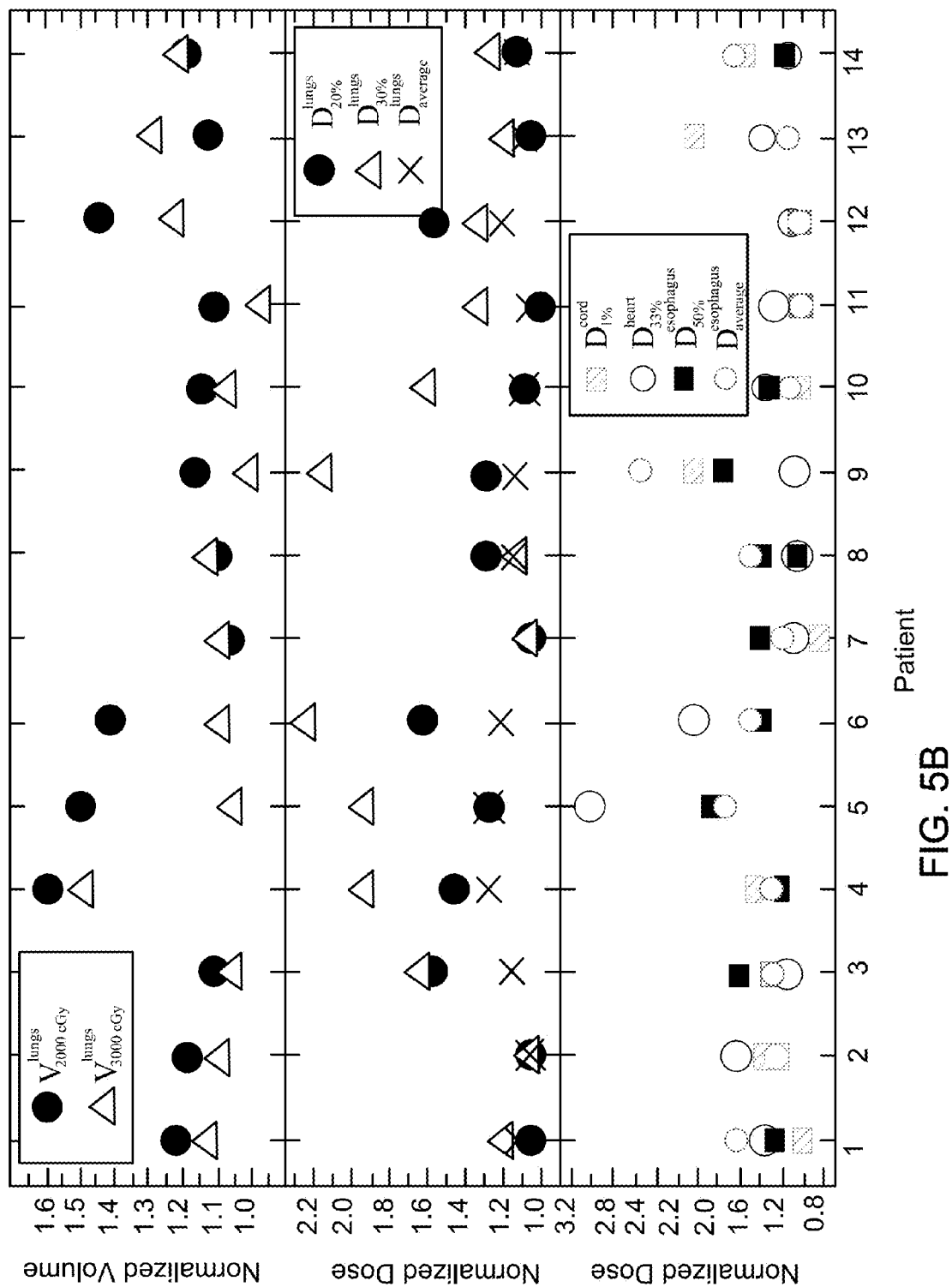
FIG. 5B is a plot illustrating normalized does indices, average doses, and isodose volumes for 12 lung cases for both volume and energy based optimization plans.

FIG. 5B is a series of plots illustrating normalized DIs and VIs differences for 14 lung cases between volume-based and energy-based optimized IMRT plans. In this case, standard deviations of the doses across the PTV are ranging from 2.7% to 4.5%, with an average 3.42% for energy-based plans, while the range for volume-based plans is from 2.8% to 4.2%, with an average of 3.65%. These findings indicate somewhat better dose homogeneity across the PTV with energy-based optimization as compared to volume-based optimization. For the critical structures, as in FIG. 5A, majority of DIs are greater than or equal to unity where in some cases they are even greater than 2. On average, over the 14 cases, the achievable sparing of ~38% for the maximum dose to the spinal cord, ~43% for one third of the heart volume, and ~33.5% to 50% of esophageal volume with energy-based optimization is achieved. The doses to 20% and 30% of the lung volumes are on average ~25.0% and 50% lower with energy-based optimization respectively. Therefore, both mass- and energy-based optimizations outperform the standard of care (i.e. volume-based optimization), with energy-based optimization resulting in significant population-based (or on average over the patient cohort) OAR sparing.

Figure 6A:
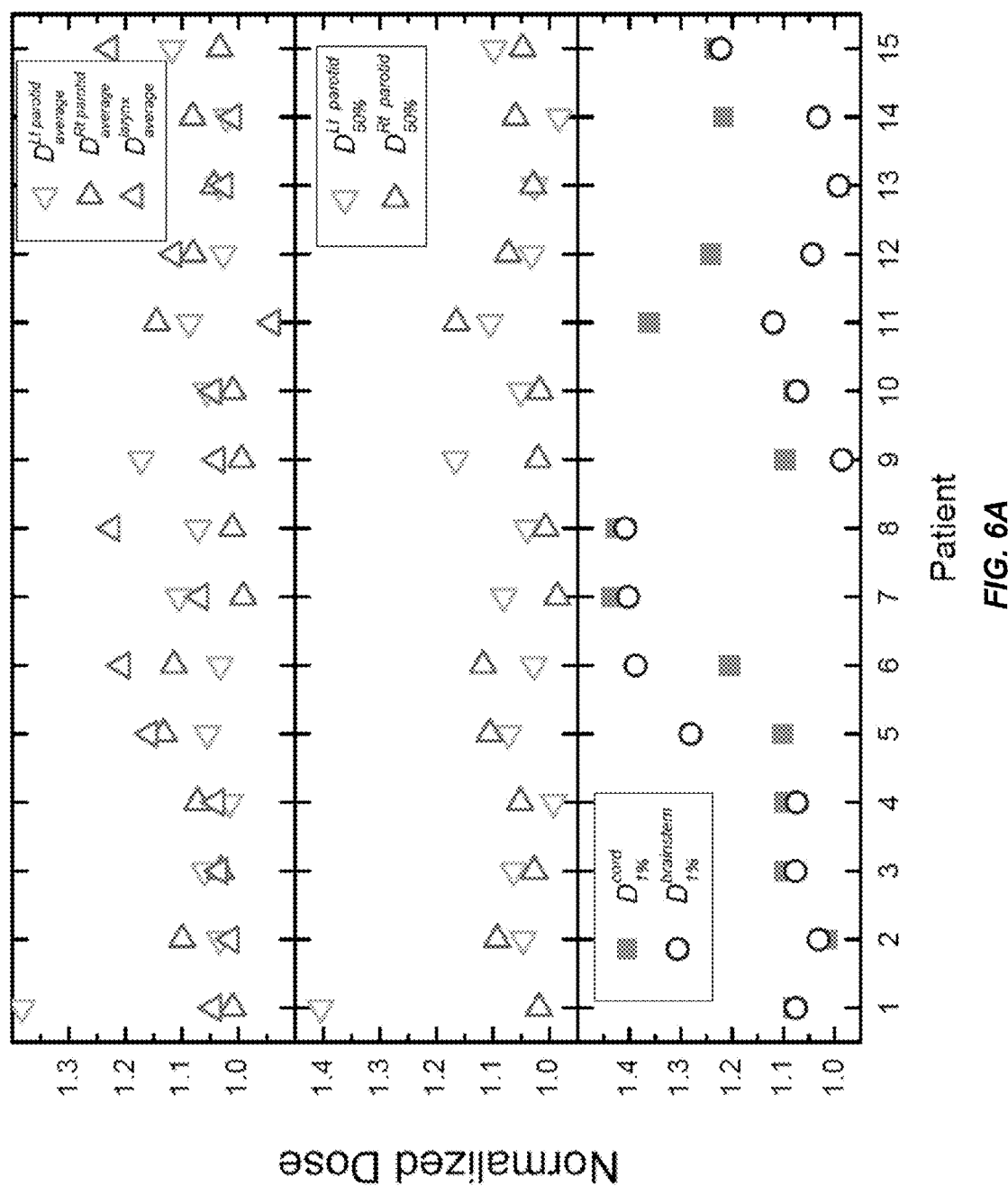
FIG. 6A is a plot illustrating normalized does indices and average doses for 15 head and neck cases with volume based and mass based optimizations.

The 15 HN cases the treatment plans, generated through volume-, mass-, and energy-based optimization, were also normalized such that 95% of the PTVs and 90% of the intermediate risk nodal volumes receive the same doses, thereby resulting in clinically equivalent therapeutic effect. Mass- and energy-based optimization was applied for all OARs when mass- or energy-based objective functions were used. The OAR results comparing volume- and mass-based optimization for the FIN cases are presented on FIG. 6A. The normalization of the DIs was been performed similarly to the normalization in FIGS. 5A and 5B. The standard deviations of the doses across the PTV are ranging from 2.9% to 4.5%, with an average 4.1% for mass-based optimization and from 2.8% to 4.5%, with an average 4.0% for volume-based optimization, indicating comparable dose homogeneity across the PTV. The bottom panel shows the doses to 1% of the cord and brainstem (used as surrogates for maximum doses), the middle panel shows the doses to 50% of the parotid glands, while the top panel shows the average doses to the parotid glands and the larynx. The average decrease in maximum dose with mass-based optimization for spinal cord and brainstem for the FIN cohort is ~18% and ~14.7% respectively. Dose to 50% of the larynx, left and right parotid volumes can be decreased as much as ~9.6%, ~7.9%, and ~5.5% respectively. The average doses to larynx and parotid volumes can be decreased between ~5.5% to ~8.5%. Therefore, in FIN cases, the population based OAR sparing with mass-based optimization is somewhat higher than in the lung cases.

Figure 6B:
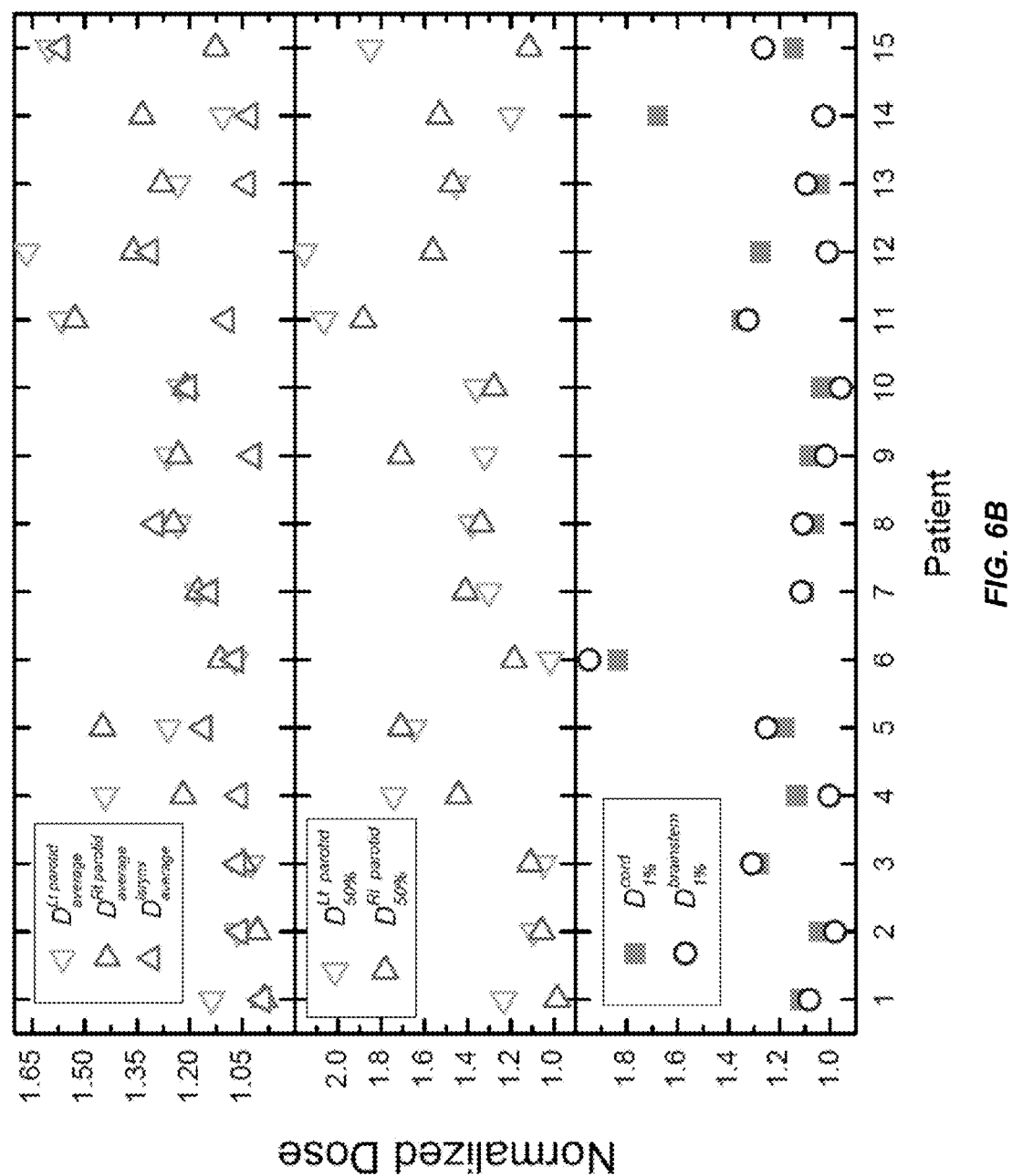
FIG. 6B is a plot illustrating normalized does indices and average doses for 15 head and neck cases with volume based and energy based optimizations.

FIG. 6B shows dose indices for FIN cases comparing volume- and energy-based optimization. The standard deviations of the doses across the PTV are ranging from 2.9% to 4.1%, with an average 3.6% for mass-based optimization and from 2.8% to 4.5%, with an average 4.0% for volume-based optimization, indicating better dose homogeneity across the PTV with energy-based optimization. For the majority of the plotted results, energy-based optimization delivers a lower dose to collateral healthy tissue than volume-based optimization. On average, the maximum cord and brainstem doses can be lowered by ~22.5% and ~16.5%. 50% of larynx and parotid volumes could receive ~17% to ~46% lower dose on average with energy-based optimization cost functions. The average doses to larynx and parotid glands can be decreased by ~14% to ~27%.

Figure 7:
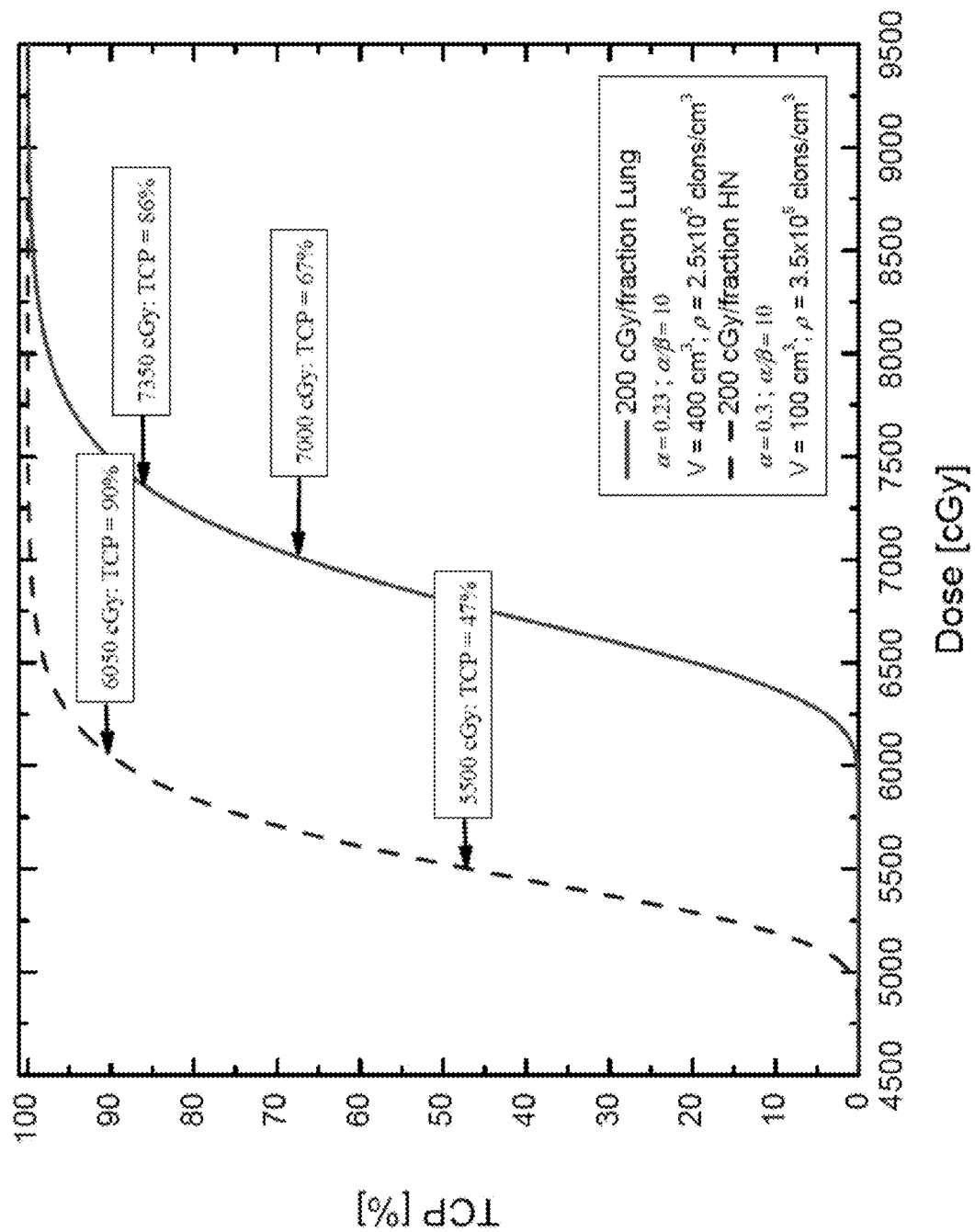
FIG. 7 is a plot illustrating sample tumor control probabilities for lung and head and neck. The calculations are based on the linear quadratic cell survival scheme with an assumption that the surviving tumor cells obey Poisson distribution.

In order to quantify the potential benefit of mass-based optimization, in terms of an isotoxic dose escalation, a tumor control probability (TCP) model is presented on FIG. 7, where only change of TCP is evaluated. FIG. 7 shows sample tumor control probability curves for lung and head-and-neck. If it is presumed that a FIN case receives 5500 cGy (volume-based optimization) with TCP of ~50%, the dose increase of ~10% (facilitated by mass-based optimization) will allow the delivery of 6050 cGy, which will result in a TCP of ~90%. Similarly, for a lung case with volume-based dose of 7000 cGy and TCP of ~67%, an increase of ~5% in dose by mass-based or energy-based optimization will result in 7350 cGy to the PTV with a TCP of ~86%. Therefore, for lung and FIN cases, based on population average results, the TCP could potentially increase with mass-based optimization by ~20% to ~40% for clinically acceptable OAR isotoxicities, compared to volume-based optimization.

Energy-based optimization application to cohorts of lung and FIN cases indicates its potential for even greater reduction of predicted OAR doses. Therefore, the estimated TCP increase with energy based optimization with respect to volume-based optimization would be larger than the estimated ~20% to ~40% in the case of mass-based optimization.

Utilization of the lower OAR doses for an isotoxic dose escalation in inverse IMRT planning can potentially boost the TCP, and therefore allow the delivery of definitive curative radiation doses for more patients. If mass- or energy-based optimization is used only for lowering the doses to OARs, then it might have a profound impact on the treatment strategy in the unfortunate event of disease recurrence and associated radiotherapy treatment at the same anatomical location.

The proposed mass-, energy-, and density-based inverse optimization treatment planning methods are applicable to radiotherapy treatments with charged (electrons, protons, heavy ions, et.) as well as uncharged (photons, neutrons) particles. The mathematical framework described herein also incorporates inverse optimization based on global energy minimization as described by equation 1. The general form of equations 1, 3, and 4 allows the use of mass based formalism not only for intensity modulation, but also for energy modulation of the incident radiation. Note that radiation dose is dependent on the energy of the incident radiation and it is natural to use this formalism for energy modulation optimization.

The present invention is not limited to IMRT applications. Embodiments of the invention provide for radiotherapy techniques such as Volumetric Modulated Arc Therapy (VMAT), 4-Dimensional, Adaptive, Real Time Adaptive, Charged Particle Modulated Therapy (IMPT), Image Guided Radiation Therapy (IGRT) and Energy Modulation may be improved by mass-based optimization. Other embodiments are within the scope of the invention.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations. Operations such as generating, determining, identifying etc., may be include calculations performed by a machine configured with a processor and memory.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, subprograms, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

It is noted that one or more references are incorporated herein. To the extent that any of the incorporated material is inconsistent with the present disclosure, the present disclosure shall control. Furthermore, to the extent necessary, material incorporated by reference herein should be disregarded if necessary to preserve the validity of the claims.

Further, while the description above refers to the invention, the description may include more than one invention.

What is claimed is:

1. A method of radiotherapy treatment planning, the method for implementation by one or more data processors forming part of at least one computing system, the method comprising:
   identifying a planned target volume for radiotherapy treatment;
   identifying at least one volume of interest;
   identifying a mass contained in at least one of the planned target volume and the at least one volume of interest;
   determining, by at least one data processor, at least one dose constraint for the planned target volume;
   determining, by at least one data processor, at least one dose constraint for the at least one volume of interest;
      wherein at least one of (a) the at least one dose constraint or an objective for the planned target volume or (b) the at least one dose constraint or an objective for the at least one volume of interest is a function of the mass;
   determining, by at least one data processor, a composite objective function using (a) the at least one dose constraint or the objective for the planned target volume, or (b) the at least one dose constraint or the objective of the at least one volume of interest; and determining, by at least one data processor, a near optimal solution to the composite objective function to produce a radiotherapy treatment plan;

wherein the function of the mass for a $j^{th}$ organ is formulated according to:

$$I_j = \sum_{i=1}^{n} D_{i,j} m_{i,j} = \sum_{i=1}^{n} D_{i,j} \rho_{i,j} v_{i,j} = \sum_{i=1}^{n} \frac{E_{i,j}}{\rho_{i,j} v_{i,j}} \rho_{i,j} v_{i,j} = \sum_{i=1}^{n} E_{i,j}$$

where $D_{i,j}$ is radiation dose, $m_{i,j}$ is the mass, $\rho_{i,j}$ is density, $v_{i,j}$ is volume, and $E_{i,j}$ is imparted energy for dose voxel i of organ j, wherein the function of the mass represents energy to be imparted by radiation to a volume of organ j.

2. The method of claim 1, wherein the radiotherapy treatment plan includes using one of: Intensity Modulated Radiation Therapy, Four Dimensional Intensity Modulated Radiation Therapy, Adaptive Intensity Modulated Radiation Therapy, Real Time Adaptive Intensity Modulated Radiation Therapy, Image Guided Intensity Modulated Radiation Therapy, or Four Dimensional Image Guided Intensity Modulated Radiation Therapy.

3. The method of claim 1, wherein the radiotherapy treatment plan includes using one of: Volumetric Modulated Arc Therapy, Four Dimensional Volumetric Modulated Arc Therapy, Intensity Modulated Charged Particle Therapy, or Four Dimensional Intensity Modulated Charged Particle Therapy.

4. The method of claim 1, wherein the radiotherapy treatment plan includes using one of: Adaptive Four Dimensional Intensity Modulated Radiotherapy, Adaptive Four Dimensional Volumetric Modulated Arc Therapy, Adaptive Four Dimensional Intensity Modulated Charged Particle Therapy, or Adaptive Four Dimensional Image Guided Intensity Modulated Radiation Therapy.

5. The method of claim 1, wherein the radiotherapy treatment plan includes using one of energy modulation for: Intensity Modulated Radiation Therapy, Four Dimensional Intensity Modulated Radiation Therapy, Volumetric Modulated Arc Therapy, Four Dimensional Volumetric Modulated Arc Therapy, Adaptive Intensity Modulated Radiation Therapy, Adaptive Four Dimensional Intensity Modulated Radiation Therapy, Adaptive Volumetric Modulated Arc Therapy, Adaptive Four Dimensional Volumetric Modulated Arc Therapy, Real Time Adaptive Intensity Modulated Radiation Therapy, Real Time Adaptive Four Dimensional Intensity Modulated Radiation Therapy, Real Time Adaptive Volumetric Modulated Arc Therapy, or Real Time Adaptive Four Dimensional Volumetric Modulated Arc Therapy.

6. The method of claim 1, wherein the radiotherapy treatment plan includes using one of: Real Time Adaptive Four Dimensional Intensity Modulated Radiotherapy, Real Time Adaptive Four Dimensional Volumetric Modulated Arc Therapy, or Real Time Adaptive Four Dimensional Intensity Modulated Charged Particle Therapy.

7. The method of claim 1, wherein the near optimal solution is a clinically acceptable solution.

8. The method of claim 1, wherein the planned target volume contains at least a portion of a tumor.

9. The method of claim 1, wherein the at least one volume of interest contains at least a portion of: an organ at risk or an anatomical structure of interest.

10. The method of claim 1, wherein the planned target volume contains at least a portion of: lung, prostate, head-and-neck, intestine, pancreas, liver, kidney, brain, bone, breast, cervix, skin, bowel, bladder, glands, colon or thyroid.

11. A non-transitory computer readable storage medium wherein code embodied in the computer readable storage medium executed by a processor performs operations, the operations comprising:

receive, by at least one data processor, data describing a planned target volume for radiotherapy treatment;

receive, by at least one data processor, data describing at least one volume of interest;

receive, by at least one data processor, data describing a mass contained in at least one of the planned target volume or the at least one volume of interest;

receive, by at least one data processor, data describing at least one dose constraint or an objective for the planned target volume;

receive, by at least one data processor, data describing at least one dose constraint or an objective for the at least one volume of interest;

wherein at least one of: (a) the at least one dose constraint or the objective for the planned target volume or (b) the at least one dose constraint or the objective for the at least one volume of interest is a function of the mass;

determine, by at least one data processor, a composite objective function using (a) the at least one dose constraint or the objective for the planned target volume, or (b) the at least one dose constraint or the objective of the at least one volume of interest; and determine, by at least one data processor, a near optimal solution to the composite objective function to produce a radiotherapy treatment plan;

wherein the function of the mass for a $j^{th}$ organ is formulated according to:

$$I_j = \sum_{i=1}^{n} D_{i,j} m_{i,j} = \sum_{i=1}^{n} D_{i,j} \rho_{i,j} v_{i,j} = \sum_{i=1}^{n} \frac{E_{i,j}}{\rho_{i,j} v_{i,j}} \rho_{i,j} v_{i,j} = \sum_{i=1}^{n} E_{i,j}$$

where $D_{i,j}$ is radiation dose, $m_{i,j}$ is the mass, $\rho_{i,j}$ is density, $v_{i,j}$ is volume, and $E_{i,j}$ is imparted energy for voxel i of organ j.

12. A system for radiation treatment planning comprising:

an input module for specifying input parameters;

wherein the input parameters comprise: a planned target volume, at least one volume of interest, a mass contained in at least one of the planned target volume or the at least one volume of interest, at least one dose constraint or an objective for the planned target volume, or at least one dose constraint or an objective for the at least one volume of interest;

wherein at least one of (a) the at least one dose constraint or the objective for the planned target volume and or (b) the at least one dose constraint or the objective for the at least one volume of interest is a function of the mass; and a processor configured to determine a composite objective function using the input parameters and to determine a near optimal solution to the composite objective function for the production of a radiotherapy treatment plan;

wherein the function of the mass for a $j^{th}$ organ is formulated according to:

$$I_j = \sum_{i=1}^{n} D_{i,j} m_{i,j} = \sum_{i=1}^{n} D_{i,j} \rho_{i,j} v_{i,j} = \sum_{i=1}^{n} \frac{E_{i,j}}{\rho_{i,j} v_{i,j}} \rho_{i,j} v_{i,j} = \sum_{i=1}^{n} E_{i,j}$$

where $D_{i,j}$ is radiation dose, $m_{i,j}$ is the mass, $\rho_{i,j}$ is density, $v_{i,j}$ is volume, and $E_{i,j}$ is imparted energy for voxel i of organ j.

13. The method of claim 1, further comprising:
   initiating the radiotherapy treatment plan using a beam forming radiotherapy treatment device.

14. The computer readable storage medium of claim 11, the operations further comprising:
   initiating the radiotherapy treatment plan using a beam forming radiotherapy treatment device.

15. The system of claim 12, further comprising a beam forming radiotherapy treatment device for performing the radiotherapy treatment plan.

* * * * *